(12) United States Patent
Link et al.

(10) Patent No.: US 9,556,470 B2
(45) Date of Patent: Jan. 31, 2017

(54) ENZYME QUANTIFICATION

(75) Inventors: Darren Link, Lexington, MA (US);
Michael L. Samuels, Windham, NH (US)

(73) Assignee: Raindance Technologies, Inc., Billerica, MA (US)

(*) Notice: Subject to any disclaimer, the term of this patent is extended or adjusted under 35 U.S.C. 154(b) by 55 days.

(21) Appl. No.: 14/122,766

(22) PCT Filed: Jun. 1, 2012

(86) PCT No.: PCT/US2012/040543
§ 371 (c)(1),
(2), (4) Date: Apr. 18, 2014

(87) PCT Pub. No.: WO2012/167142
PCT Pub. Date: Dec. 6, 2012

(65) Prior Publication Data
US 2014/0295421 A1    Oct. 2, 2014

Related U.S. Application Data

(60) Provisional application No. 61/492,602, filed on Jun. 2, 2011.

(51) Int. Cl.
*C12Q 1/25* (2006.01)
*B01F 5/06* (2006.01)
(Continued)

(52) U.S. Cl.
CPC ............... *C12Q 1/25* (2013.01); *B01F 3/0807* (2013.01); *B01F 5/0646* (2013.01); *B01F 5/0653* (2013.01); *B01F 13/0062* (2013.01); *B01J 19/0046* (2013.01); *B01L 3/502761* (2013.01); *C40B 40/04* (2013.01); *C40B 50/08* (2013.01); *C40B 60/10* (2013.01); *G01N 33/5008* (2013.01); *B01J 2219/0059* (2013.01); *B01J 2219/0065* (2013.01); *B01J 2219/0072* (2013.01); *B01J 2219/0074* (2013.01); *B01J 2219/00286* (2013.01); *B01J 2219/00351* (2013.01); *B01J 2219/00418* (2013.01); *B01J 2219/00479* (2013.01); *B01J 2219/00576* (2013.01); *B01J 2219/00585* (2013.01);
(Continued)

(58) Field of Classification Search
CPC .............. B01J 2219/00599; B01J 2219/00657; B01J 2219/00722; B01J 2219/00576; B01J 2219/00418; B01J 2219/00286; B01J 2219/00479; B01L 2300/0864; B01L 2400/0415; B01L 2200/027; G01N 21/6445
See application file for complete search history.

(56) References Cited

U.S. PATENT DOCUMENTS

| | | | |
|---|---|---|---|
| 2002/0058332 A1* | 5/2002 | Quake | B01L 3/502784 435/288.5 |
| 2008/0014589 A1* | 1/2008 | Link et al. | 435/6 |
| 2010/0022414 A1* | 1/2010 | Link | B01F 3/0807 506/18 |

* cited by examiner

*Primary Examiner* — Rebecca Martinez
(74) *Attorney, Agent, or Firm* — Brown Rudnick LLP; Adam M. Schoen

(57) ABSTRACT

The invention generally relates to methods for quantifying an amount of enzyme molecules. Systems and methods of the invention are provided for measuring an amount of target by forming a plurality of fluid partitions, a subset of which include the target, performing an enzyme-catalyzed reaction in the subset, and detecting the number of partitions in the subset. The amount of target can be determined based on the detected number.

25 Claims, 36 Drawing Sheets

(51) Int. Cl.
  *B01J 19/00*      (2006.01)
  *B01F 13/00*      (2006.01)
  *B01L 3/00*       (2006.01)
  *B01F 3/08*       (2006.01)
  *C40B 40/04*      (2006.01)
  *C40B 50/08*      (2006.01)
  *C40B 60/10*      (2006.01)
  *G01N 33/50*      (2006.01)
  *B01L 7/00*       (2006.01)
  *G01N 21/64*      (2006.01)

(52) U.S. Cl.
  CPC ............... *B01J 2219/00592* (2013.01); *B01J 2219/00599* (2013.01); *B01J 2219/00657* (2013.01); *B01J 2219/00664* (2013.01); *B01J 2219/00702* (2013.01); *B01J 2219/00722* (2013.01); *B01J 2219/00743* (2013.01); *B01L 7/52* (2013.01); *B01L 2200/027* (2013.01); *B01L 2300/0636* (2013.01); *B01L 2300/0645* (2013.01); *B01L 2300/0654* (2013.01); *B01L 2300/0681* (2013.01); *B01L 2300/0864* (2013.01); *B01L 2300/0867* (2013.01); *B01L 2400/0415* (2013.01); *B01L 2400/0487* (2013.01); *G01N 21/6428* (2013.01); *G01N 21/6445* (2013.01); *G01N 2500/00* (2013.01)

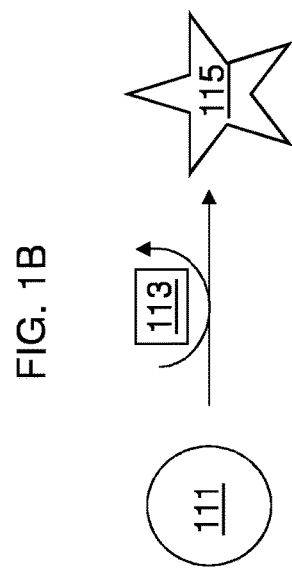
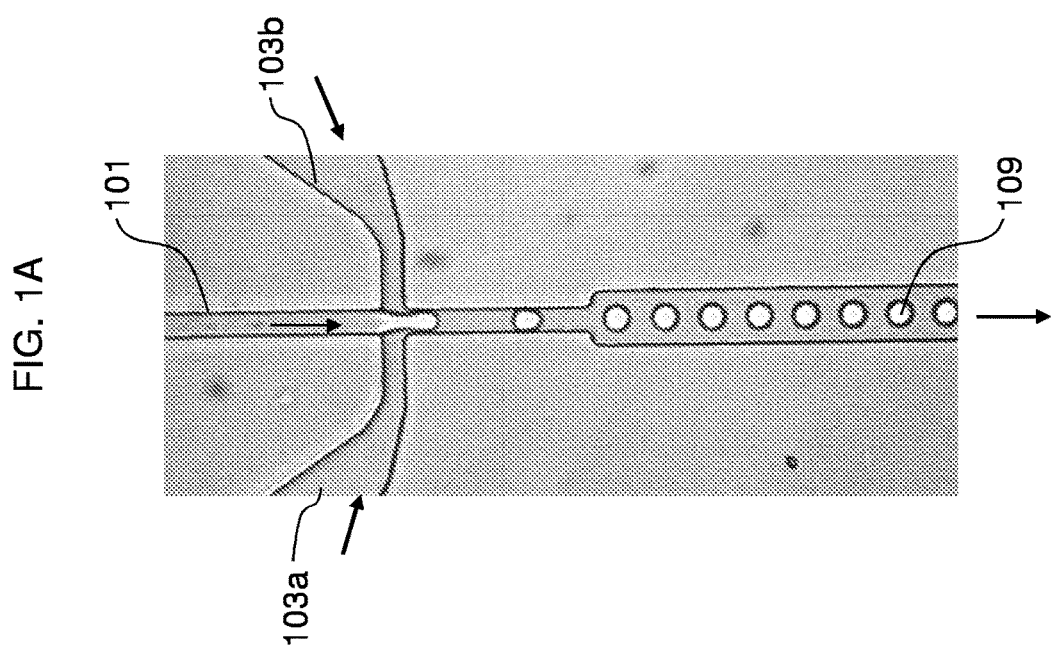

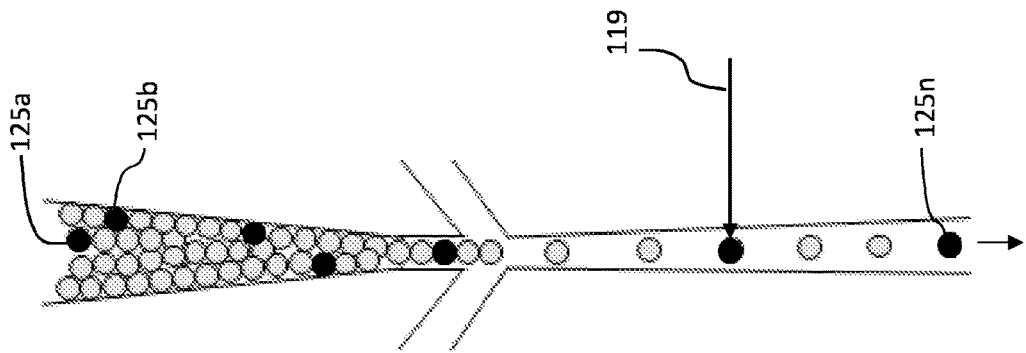
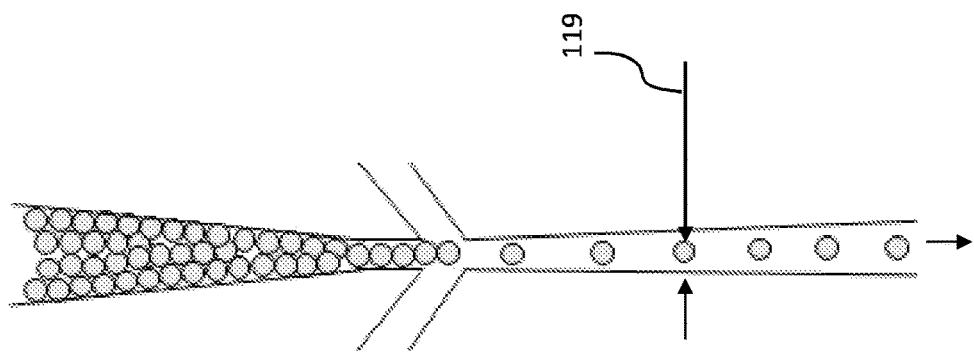
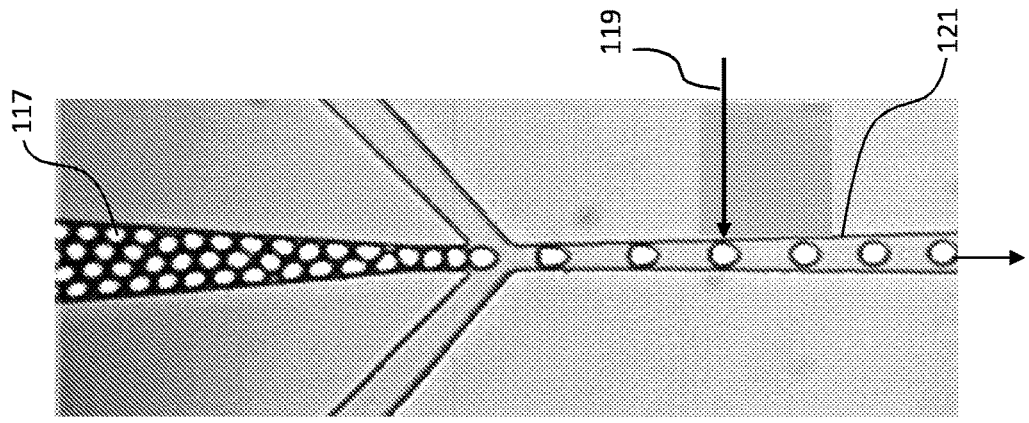

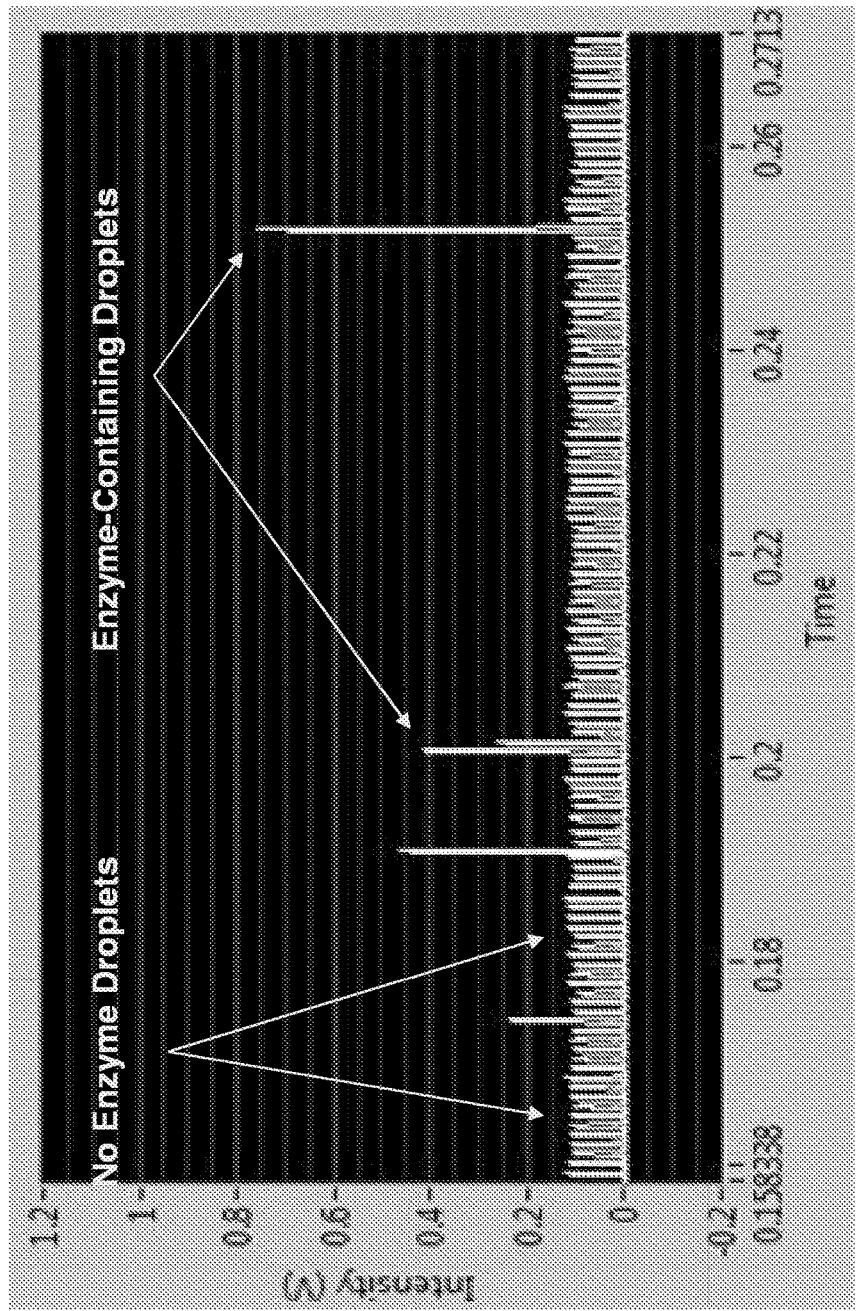

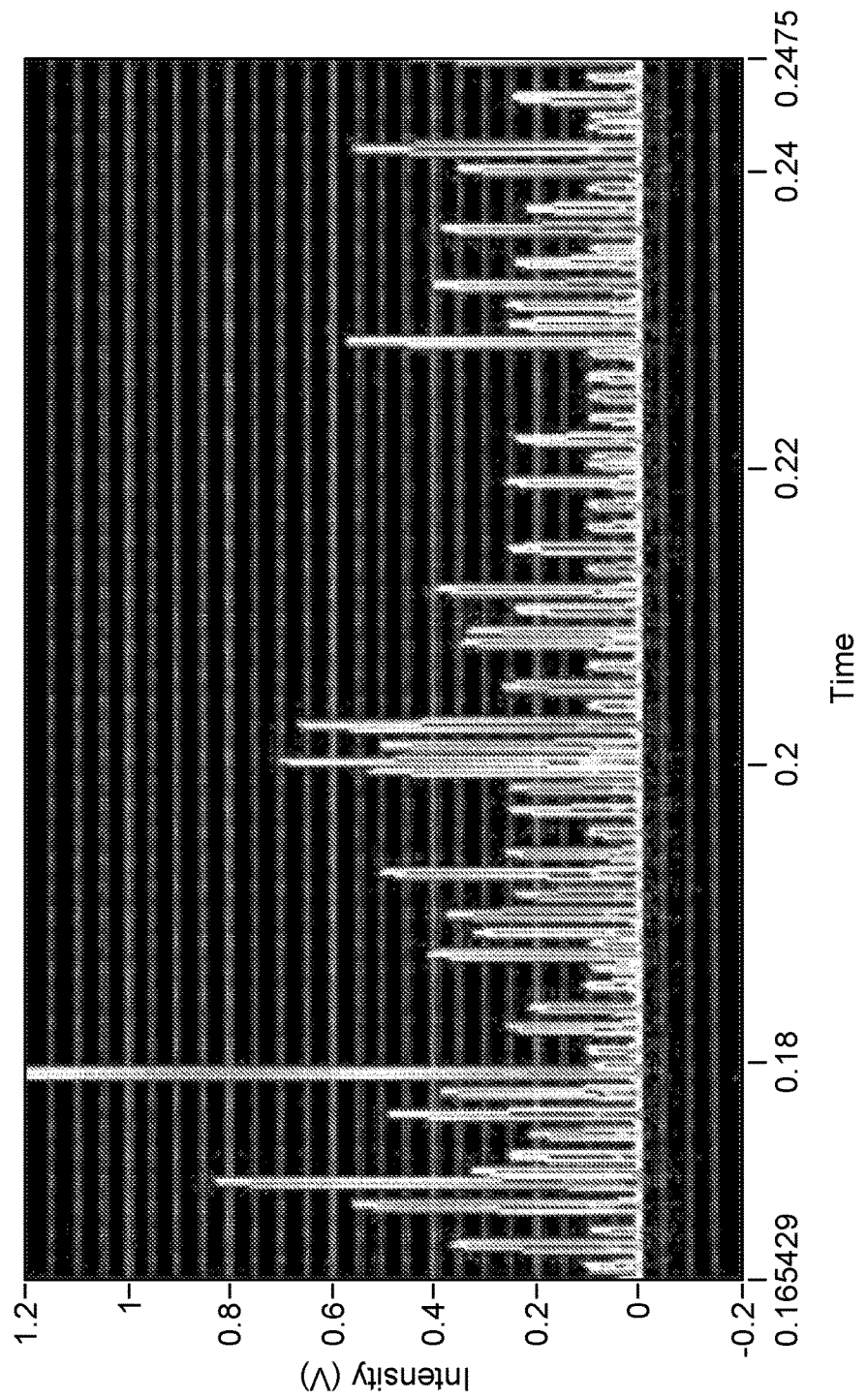

Calculated Concentration = 0.064 pM

Fluorescence Measured Per Molecule

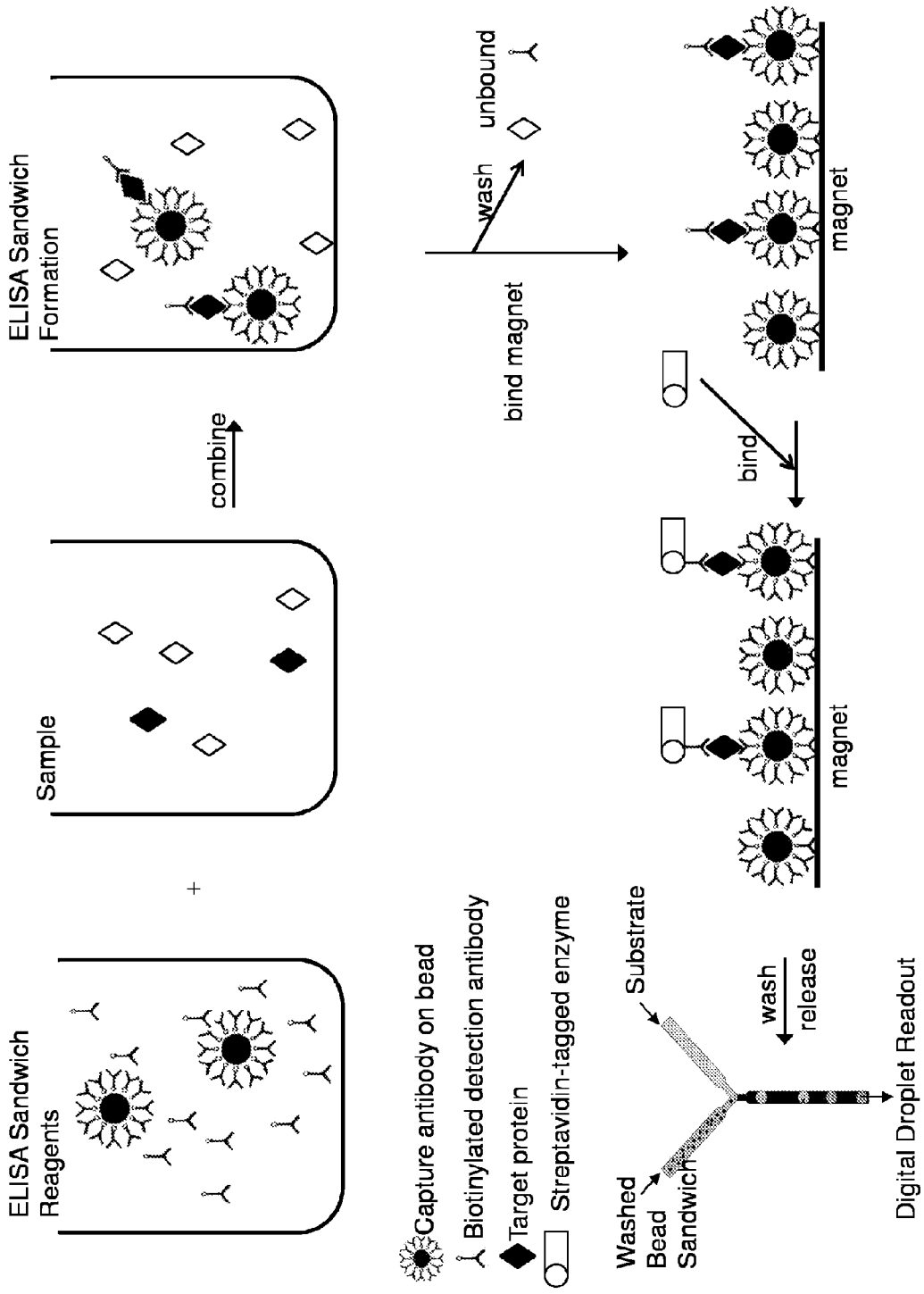

Single bead, single bound enzyme

Multiple beads, single bound enzyme

Released single enzyme

Released antibody, single bound enzyme

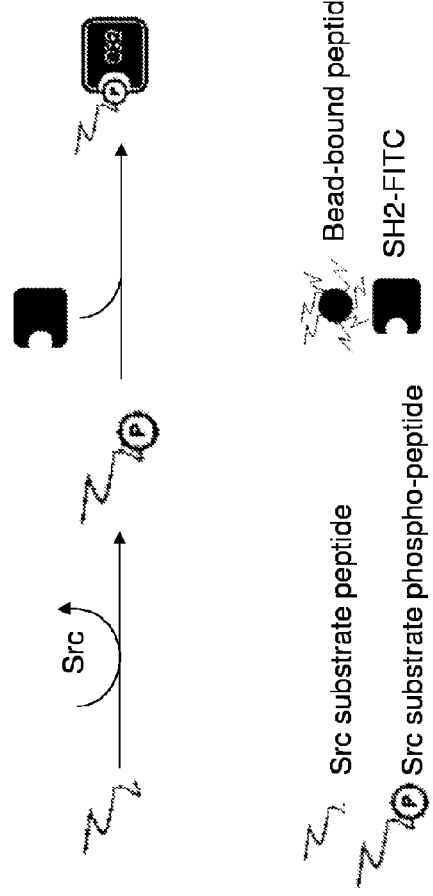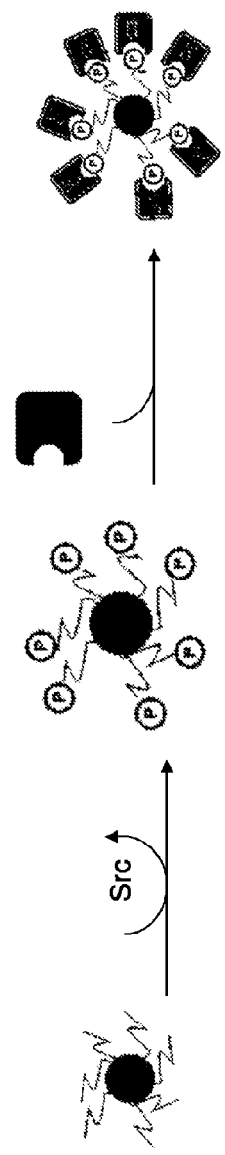
FIG. 8A
FIG. 8B

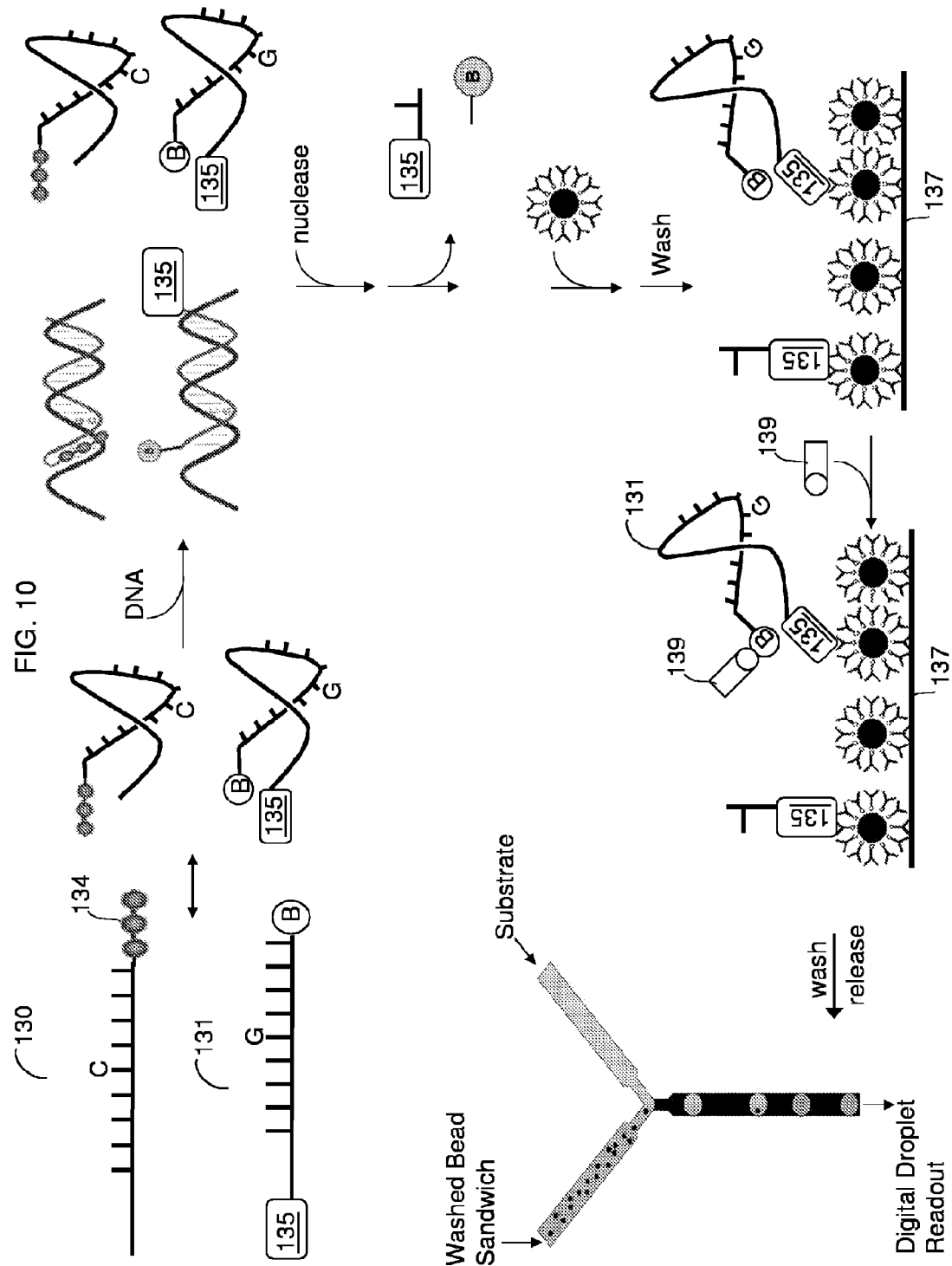

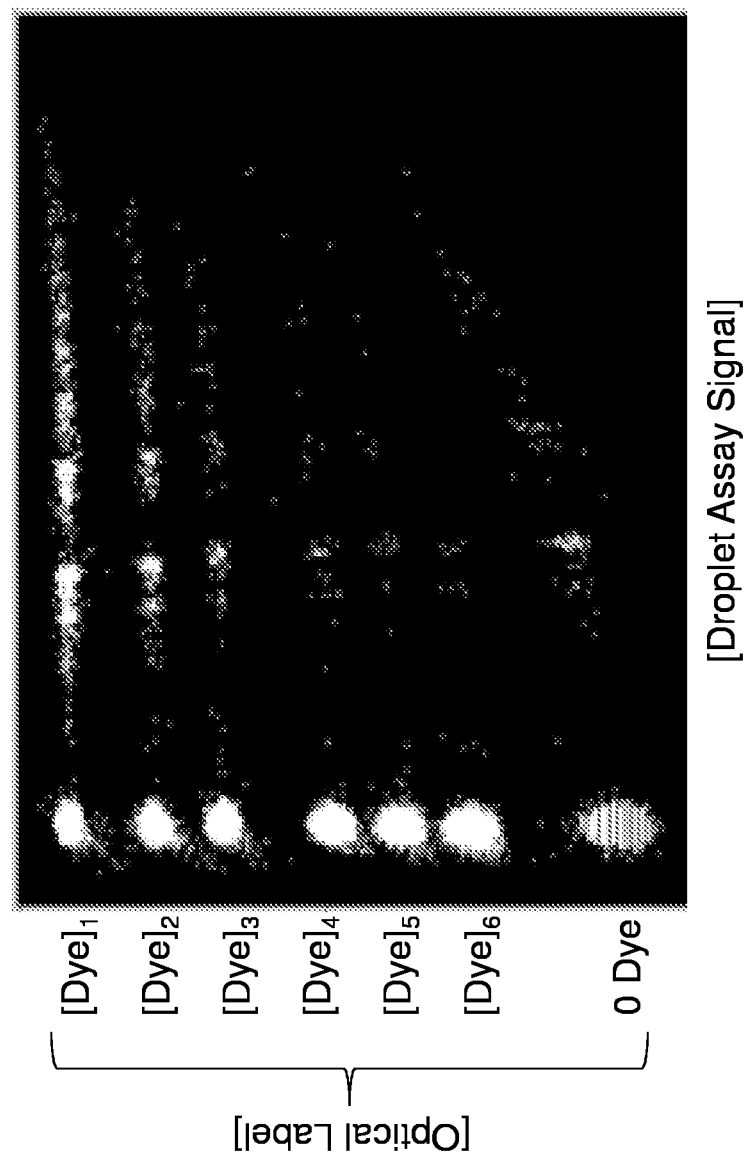

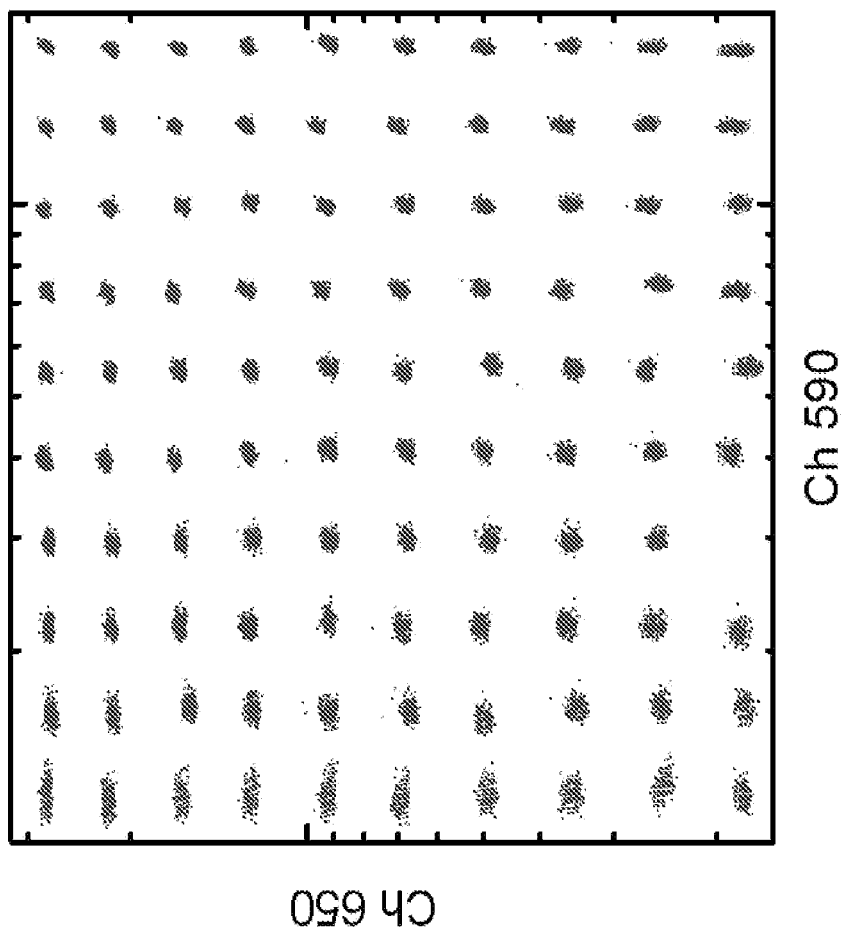

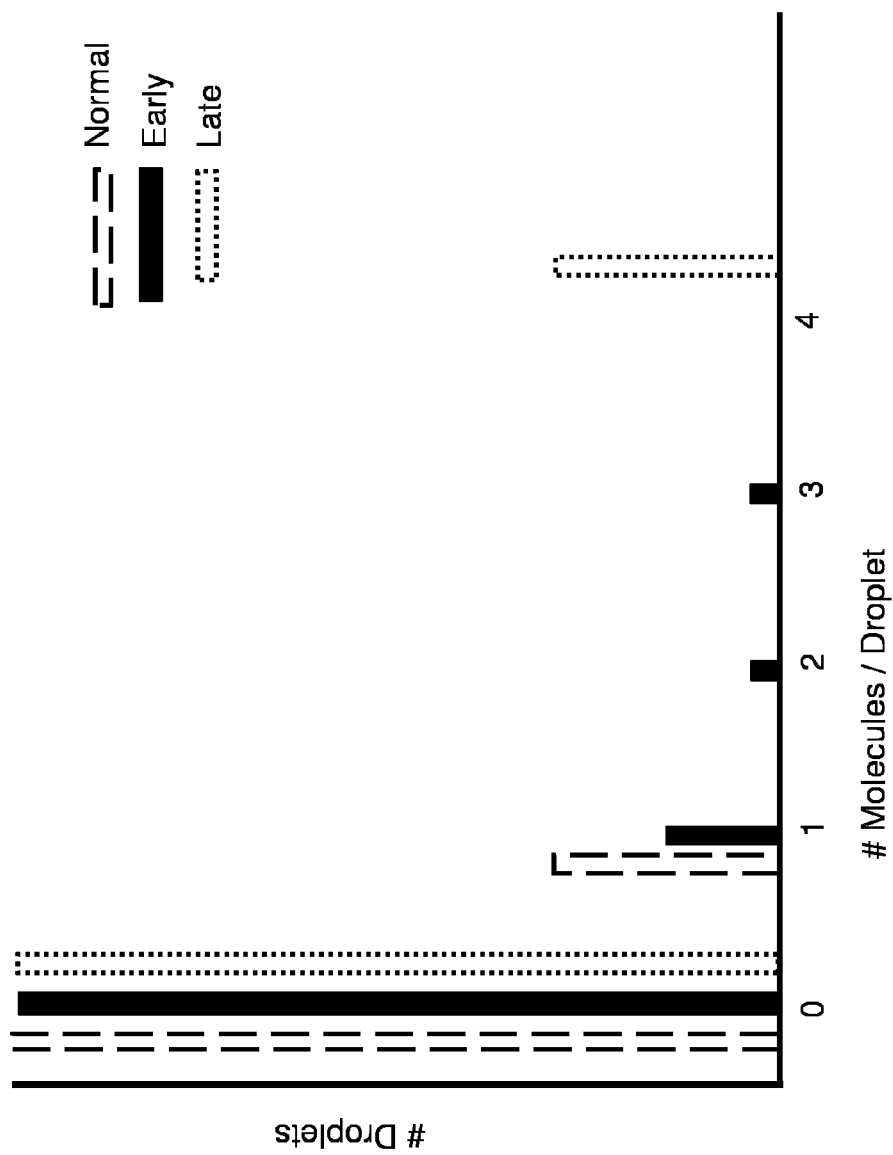

ENZYME QUANTIFICATION

CROSS-REFERENCE TO RELATED APPLICATION

This application is a 35 U.S.C. §371 national phase patent application of PCT/US2012/040543, filed Jun. 1, 2012, which claims the benefit of and priority to U.S. Provisional Patent Application No. 61/492,602, filed on Jun. 2, 2011, the contents of each of which are hereby incorporated by reference in their entirety.

FIELD OF THE INVENTION

The invention generally relates to methods for quantifying an amount of enzyme molecules.

BACKGROUND

Enzyme assays are used to measure enzymatic activity, which is a measure of the quantity of active enzyme present in a reaction. Enzyme assays are important when analyzing enzyme kinetics and enzyme inhibition. Enzyme kinetics relates to chemical reactions that are catalyzed by enzymes. In enzyme kinetics, the reaction rate is measured and the effects of varying the conditions of the reaction investigated. Enzyme kinetics reveal the catalytic mechanism of an enzyme, its role in metabolism, how its activity is controlled, and how a drug or a poison might inhibit the enzyme.

SUMMARY

This invention provides methods to identify and quantify the presence, type, and amount of reactants and products of chemical reactions. The invention takes advantage of the ability to form discrete droplets that contain the components of a chemical reaction. Because measurements can be performed on individual droplets and collections of individual droplet, it is possible to identify and quantify chemical reaction components in the droplets according to methods described herein. Methods of the invention are useful to detect and/or quantify any component of a chemical reaction. In one preferred embodiment, enzyme molecules are quantified based on their activity inside individual droplets. In order to identify and quantitate enzyme activity, droplets are identified as "negative" and/or "positive" droplets for the reaction catalyzed by the target enzyme, and the number of enzyme molecules within positive droplets (e.g., based on the quantized signal strength) is determined. Digital counting of enzyme molecules provides an extremely wide dynamic range of detection, with a lower limit of detection dependent on the number of molecules available to count and the total number of droplets read (e.g. 1 in $10^7$, in one hour using a droplet flow rate of $10^7$ per hour) and the upper limit for single molecule counting determined by the number of droplets but also includes a further range where multiple or average numbers of molecules are present in droplets.

In general, the invention involves incorporating components of a chemical reaction in a droplet and allowing the chemical reaction to occur in the droplet. One or more of the components of the reaction is detectably labeled (e.g., with a reporter molecule) such that label is detectable as a result of the reaction (e.g., release of a reporter). Detection and quantification of the label allows detection and quantification of the reaction components. The reporter moiety may be any detectable moiety that can be used as an indicator of reaction components (e.g., enzyme activity). Any reporter system known in the art may be used with methods of the invention. In certain embodiments, the reporter moiety is a fluorescent moiety.

In a preferred embodiment, a reporter is attached to one or more substrate(s) of a chemical reaction in a droplet, which label is released upon enzymatic catalysis. The number of droplets containing quantified enzyme molecules are then determined based upon the presence and/or signal strength of the reporter. Reporter (and therefore enzyme) can be quantified based upon these measurements as well. Methods of the invention involve forming a sample droplet. Any technique known in the art for forming sample droplets may be used with methods of the invention. An exemplary method involves flowing a stream of sample fluid so that the sample stream intersects one or more opposing streams of flowing carrier fluid. The carrier fluid is immiscible with the sample fluid. Intersection of the sample fluid with the two opposing streams of flowing carrier fluid results in partitioning of the sample fluid into individual sample droplets. The carrier fluid may be any fluid that is immiscible with the sample fluid. An exemplary carrier fluid is oil, which may in some cases be fluorinated. In certain embodiments, the carrier fluid includes a surfactant, such as a fluorosurfactant.

In some aspects, the invention provides methods for digital distribution assays that allow, for example, for detection of a physiological condition in a human. Detectable physiological conditions include conditions associated with aggregation of proteins or other targets. Methods include forming fluid partitions that include components of a detectable chemical reaction and conducting the reaction. A distribution of at least one of the components is determined based on detecting the detectable reaction. A statistically expected distribution can be computed and compared to the determined distribution or comparisons of distributions from known or typical samples. Based on these comparisons, the presence and/or the severity of the potential condition can be determined. In certain embodiments, the condition involves protein aggregation. The protein can be a protein from a sample from a patient. In some embodiments, methods assay for Alzheimer's disease, Parkinson's disease, Huntington's disease, Type II diabeties mellitus, prion-associated diseases, or other conditions.

Another droplet formation method includes merging at least two droplets, in which each droplet includes different material. Another droplet formation method includes forming a droplet from a sample, and contacting the droplet with a fluid stream, in which a portion of the fluid stream integrates with the droplet to form a droplet. An electric field may be applied to the droplet and the fluid stream. The electric field assists in rupturing the interface separating the two fluids. In particular embodiments, the electric field is a high-frequency electric field.

Methods of the invention may be conducted in microfluidic channels. As such, in certain embodiments, methods of the invention may further involve flowing the droplet channels and under microfluidic control.

BRIEF DESCRIPTION OF THE DRAWINGS

FIGS. 1A-1G show droplet formation and detection of reaction positive droplets.

FIGS. 2A-2D show readouts of time traces at different enzyme concentrations. Time traces show digital reactions in droplets at low enzyme concentrations.

FIG. 5 is a schematic showing sandwich formation for digital droplet ELISA.

FIGS. 8A and 8B show fluorescent polarization as another mode for readout.

FIG. 10 is illustrates a digital competitive allele specific enzyme (CASE) assay.

FIGS. 11A-11C show multiplexing embodiments.

FIG. 19 is a diagram of results of a digital distribution assay.

DETAILED DESCRIPTION

Figure 1F:
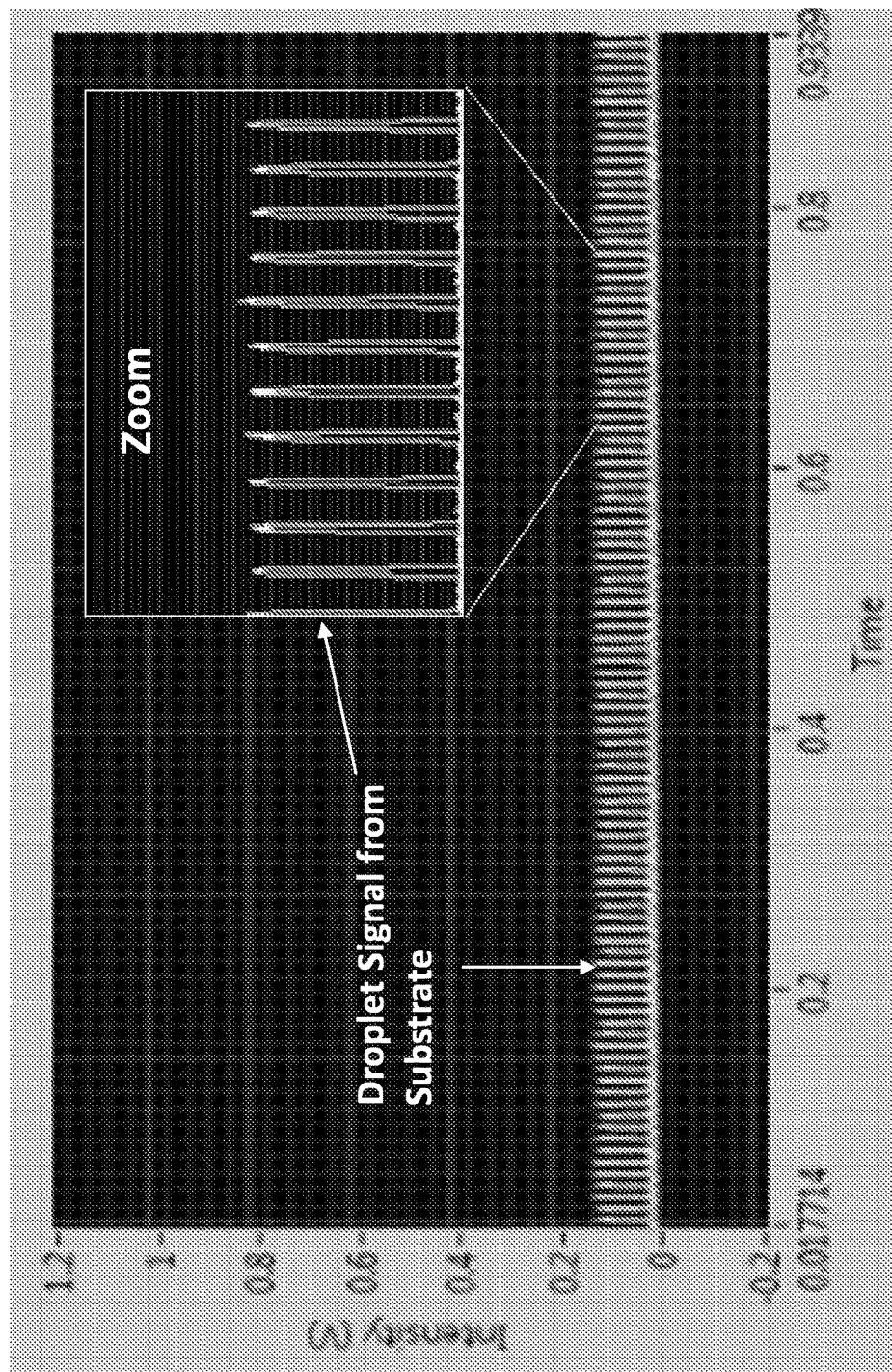

Described herein are methods for counting enzyme molecules in fluid partitions such as, for example, microdroplets. A number of readout modes and multiplexing formats are illustrated, and examples of assays coupled to the digital readout are shown.

In some embodiments, methods of the invention include a sandwich immunoassay, allowing for absolute counting of protein molecules in a sample (digital droplet ELISA). Any upfront assay that uses a chemical reaction at least one component of which includes a detectable label (e.g., a reporter enzyme system) can be used. Any suitable detectable label may be included (e.g., a fluorescent product, or other optical or detectable non-optical product) can be used with methods of the invention.

In certain embodiments, the invention provides methods for the direct detection and quantification of enzymatically active molecules potentially contained in samples (e.g., "bio-prospecting"). Reporter substrates specific for the target enzyme or enzyme class are used to assay for enzyme-containing samples (or coupled enzyme and substrates report to report on another enzyme molecule). For example, a sample can be obtained that is suspected to contain a target molecule of interest or a target molecule member of a class of interest. The sample can be distributed into a plurality of fluid partitions. Further, where a specific activity or moiety is of interest or if enzymes having a range or threshold of specific activity are of interest, a large number of targets can be assayed using methods and systems of the invention. The targets can be distributed among a plurality of fluid partitions, and each partition can be provided with reagents for a certain enzyme-catalyzed reaction. The occurrence of the reaction in certain partitions can be detected. Optionally, using sorting methods, enzyme-positive partitions can be isolated for further analysis. Thus, a single (or very low amount of) target, even an unknown target, can be identified and isolated according to activity. Further discussion can be found in Miller, et al., PNAS 109(2):378-383 (2012); Kiss, et al., Anal. Chem. 80(23):8975-8981 (2008); and Brouzes, et al., Droplet microfluidic technology for single-cell high-throughput screening, 10.1073/PNAS.0903542106 (Jul. 15, 2009), the contents of which are hereby incorporated by reference in their entirety.

Methods of the invention allow for the detection of two or more enzyme molecules or other molecules in a complex that can be assayed using an enzymatic reporter or other activatable and readable reporter (e.g. protein aggregation assay for mis-folded or disease associated molecules). Methods include providing separately detectable substrates for each enzyme species or where complexes/aggregates are detected by different product concentrations using the same enzyme type. A complex can be detected as both product signals are detected in the same fluid partition even when the fractional occupancy is low. For example, at very low fractional occupancies, there is a vanishing probability of the two enzymes being found in some number of the same fluid partitions if not in a complex together (modeled according to Poisson statistics). Thus, the detection of both product signals reveals a protein-protein interaction between the two enzymes.

A number of examples are shown utilizing 'endpoint' type digital counting, where the enzymatic reaction has reached a plateau. More than one endpoint can also be used for detection of multiple species. The invention further includes measurements at earlier time points during the reaction ('kinetic' measurements vs. 'endpoint' measurements) such that different signal intensities from single enzyme molecules reflect differences in enzymatic specific activity, the presence of inhibitory or activating molecules, or the presence of more than one enzyme molecule per droplet. Kinetic mode measurements can be made following droplet incubation at the appropriate temperature either off chip or on chip. For on-chip measurements, a 'timing module', such as a delay line, can be used to keep droplets on-chip for an appropriate length of time, and one or multiple measurement points along the length of the microfluidic channel can enable very precise kinetic measurements. A delay line can include, for example, a channel in a chip through which droplets flow. A delay line may include locations for stopping droplets, or locations for moving droplets out of the may stream of flow, or locations for droplets to separate from the oil by buoyancy differences between the oil and the droplets. A delay line may include a means of adding or removing oil to speed up or slow down the rate of travel of droplets through the delay line. A delay line may include neck-downs or other features to homogenize the average velocity of the droplets and minimize dispersion effects as droplets travel through the channel. A droplet trap may be utilized to trap droplets for a fixed period of time before releasing the droplets. Such a trap may include a valve, or require the reversal of the direction of flow through the trap region to release the trapped droplets or it may require that the chip be flipped over to reverse the direction that the droplets move in the gravitational field. One skilled in the art will recognize a number of ways to control the timing of the reaction. A portion of the channel may have a much broader cross-sectional area that upstream or downstream portions. Thus, for a certain volume per time flow rate, the distance per time flow rate in the broad portion will be much slower. Working with fluidic chips and known droplet behaviors, a channel can be designed with a delay line that delays the flow for a predetermined amount of time. This can allow reactions to incubate or progress for the appropriate amount of time. Temperature control of specific regions may be included in chip designs and interfaces with the chips.

Analyte or reporter molecule may also include non-enzyme species, provided the molecule or complex participates in generation of a readable signal (e.g. an enzymatic activator or inhibitor).

In general, the invention provides methods and systems for measuring a molecular target. A plurality of fluid partitions are formed. Fluid partitions can be any known in the art such as, for example, wells on a plate or water-in-oil droplets. A detectable reaction, such as an enzyme-catalyzed reaction, is performed in some subset of the fluid partitions. For example, where a sample suspected of containing the molecular target is separated into the fluid partitions (including via an optional dilution or serial dilution step), the subset of partitions that contain the target will include a certain number of partitions. That number can be associated with the amount of target in the sample.

A detectable reaction occurs in the subset of partitions that contain the molecular target. In some embodiments, the molecular target is an enzyme, and all of the partitions are provided with a fluorescently labeled substrate. The enzyme-catalyzed reaction can release the fluorescent label from the substrate such that the fluor becomes un-quenched or can be quantified by its location in the partition. In certain embodiments, the target is a substrate, and all of the partitions are provided with an enzyme and optionally an additional substrate or a co-factor. One of the reaction ingredients contains a molecular label that is released when the reaction occurs.

Because a productive reaction only takes place within the subset of partitions that contain the target, determining the number of partitions within which the reaction takes place (i.e., determining the number of the subset) allows one to determine the amount of target in the original sample. Since each partition is counted as reaction-positive or reaction-negative (e.g., in the subset or not), this detection is said to be digital. This includes cases where the positives can be further quantified as containing quantized numbers of targets.

In certain embodiments, digital detection operates through a reaction that includes a number of stages including, in various embodiments, enzymes that are themselves substrates for other enzyme-catalyzed reactions and substrates and/or enzymes or targets that are dark (i.e., not reporting) when participating in reactions and that are detectable when not. To illustrate, in certain embodiments, a partition includes an enzyme and a substrate which together will report the presence and number of target molecules. The substrate is labeled such that it gives a dark state as long as the enzyme is present. A target molecule that inhibits the enzyme can be assayed for according to the steps described herein. Since the target inhibits the reporting enzyme, then presence of the target will cause the reporter to generate a readable signal.

In certain embodiments, a substrate is included in a reaction mixture along with an enzyme that catalyzes a readable reaction of the substrate, but the included enzyme is in an inactive form and exposure of the included enzyme to the target molecule will catalyze its conversion to an active form. In this fashion, the presence or absence of target initiates an enzyme cascade that results in a readable assay (the cascade can include multiple steps) and quantified. In one embodiment, an apoenzyme is used to detect the presence of a protease. The apoenzyme is provided in a fluid partition with a substrate of the active form of the enzyme. The apoenzyme will only be cleaved to form the active form if the protease is present in the target sample.

The invention further provides methods and systems for detecting or quantifying the presence of an enzyme inhibitor or activator. For example, fluid partitions can be provided with an enzyme and its substrate. A sample suspected to contain an inhibitor or activator is separated into the partitions (with optional dilution). Release of a reporter via an enzyme catalyzed activity indicates the presence of an activator or absence of an inhibitor. Further, enzyme kinetics as well as inhibition or activation can be studied with methods described herein.

Methods of the invention can be used with any suitable enzyme(s) or substrate(s). For example, beyond the variety of examples given herein, the invention can further be used to detect cleavage of a peptide by a protease. Where a sample is suspected to contain a protease, a fluorescently labeled peptide substrate can be provided in the fluid partitions.

As another example, methods of the invention can include use of a polymerase enzyme and fluorescently labeled nucleotides to detect activity of a ligase. Given the appropriate conditions, the polymerase will only act on a product of a reaction catalyzed by the ligase (e.g., a polynucleotide). When the polymerase catalyzes a reaction it releases the fluorescent reporter as a readable signal.

In one other illustrative example, the presence, type, and number of restriction enzyme(s) can be quantified by providing a construct that includes an oligonucleotide with a fluor and a quencher close enough to each other that the quencher quenches the fluor but is separated by a restriction site. The presence of the restriction enzyme in the target sample will light up what is otherwise a dark fluid partition. The presence, type, and number of a set of analytes can be assayed using restriction enzymes that are specific for different readable substrates, or can be configured into a 'one-of-many' type of assay where all the analytes have the same restriction enzyme and substrate, or can be grouped into different classes using enzyme/substrate classes.

In certain embodiments, the invention provides systems and methods for detecting and quantifying classes of enzymes or substrates. Any class of target can be the subject of an assay including, for example, all enzymes exhibiting a certain activity or all enzymes in a certain taxonomic group.

Another embodiment includes a downstream reporter that is split (e.g., split green fluorescent protein or a split enzyme reporter) into multiple parts that do not interact productively in the absence of the upstream reporter (e.g. cleavage of the modified downstream reporter by the upstream reporter enzyme-oligo-modified reporter activated by the action of a restriction enzyme or a peptide-modified reporter activated by protease reporter), or that require being brought into close proximity for activity (e.g. following cleavage of the inhibiting modification, two halves of a split enzyme are brought into proximity for folding and activation). Two subsections of the reporter can be separated by an oligo containing a restriction site such that if the restriction enzyme (or, remembering that an enzyme can in turn be a substrate for another enzyme, an enzyme that activates the restriction enzyme) is present, the oligo is cleaved and the two subsections can come together to form the active reporter. Alternatively, cleavage of linked moieties can release inhibition of an activity that produces a readable signal.

One of skill in the art will recognize that any number of the examples given herein can be combined to create multistep assays. Thus, for example, a restriction enzyme can cleave an oligo that is separating two halves of a protease. The active protease can cleave an apoenzyme to release an active phosphorylase that phosphorylates and de-activates a downstream enzyme. If the downstream enzyme is an inhibitor of a final enzyme, then deactivation of a downstream enzyme can result in activity of the final enzyme. One of skill in the art will recognize the wide variety of combinations of the scenarios given herein that can be used.

FIGS. 1A-1G show a workflow example for a digital droplet reporter enzyme assay. In FIG. 1A, the enzyme molecules to be counted are mixed with a fluorogenic substrate and loaded into droplets via introduction into a microfluidic nozzle. The aqueous mixture of enzyme and substrate flows down inlet channel 101 and forms an emulsion when merged with oil from carrier fluid channels 103a and 103b. In FIG. 1A, arrows indicate the direction of flow. The co-infusion of an immiscible oil segments the aqueous stream into a number of uniformly sized droplet 109.

The droplet emulsion is collected into a suitable container for off-chip incubation at an appropriate temperature for enzymatic function.

FIG. 1B illustrates a schematic overview of a reaction according to certain embodiments of the invention. In general, as shown in FIG. 1B, an enzyme 113 catalyzes the conversion of a fluorogenic substrate 111 to a fluorescent product 115.

In one exemplary embodiment, enzyme 113 was streptavidin-conjugated beta galactosidase (β-gal) (Calbiochem product #569404 from Merck KGaA (Darmstadt, Germany)) and fluorogenic substrate 111 was fluorescein di-β-D-galactopyranoside (FDG) sold under the trademark MOLECULAR PROBES as product number F1179 by Life Technologies (Carlsbad, Calif.), with active enzyme able to cleave the substrate to release, as fluorescent product 115, fluorescein isothiocyanate (FITC) and two galactose.

As shown in FIG. 1C, after incubation of the droplet emulsion at 37° C. for a determined time, the droplet temperature can be changed such that the enzyme is no longer affecting the readable signal, and the droplets can be infused into a second microfluidic nozzle 117, spaced into a train of individual droplets using an immiscible oil, and run past laser spot 119 focused in microfluidic channel 121. FIG. 1D is an illustration depicting the detection step when no enzyme is present (or after enzyme is loaded but before incubation). The droplets in FIG. 1D all exhibit uniformly low fluorescence intensity, indicating a lack of conversion of substrate 111 to product 115.

As discussed with reference to FIGS. 1C-1E, detection can include droplets flowing past a detector. However, any suitable method of detecting an enzymatic reaction in a fluid partition can be used including, for example, optical or non-optical detection such as pH change or change in impedance or conductivity within a fluid partition, or any other suitable detection method. In some embodiments, non-optical detection includes nuclear magnetic resonance (NMR) analysis of materials from fluid partitions. Detection after release of the digitally generated reporter moieties from the partitions may also be used (e.g. array, electrode, magnet, sequencer, mass spectrometer, other methods).

FIG. 1E is an illustration depicting the detection step when a low concentration of enzyme is present, after incubation. Laser spot 119 is used to detect a number n of positive droplets 125a, 125b, . . . , 125n. By counting the results of laser detection, the number of partitions (here, droplets) in the subset of partitions in which an enzyme-catalyzed reaction occurred is determined.

Figure 1G:
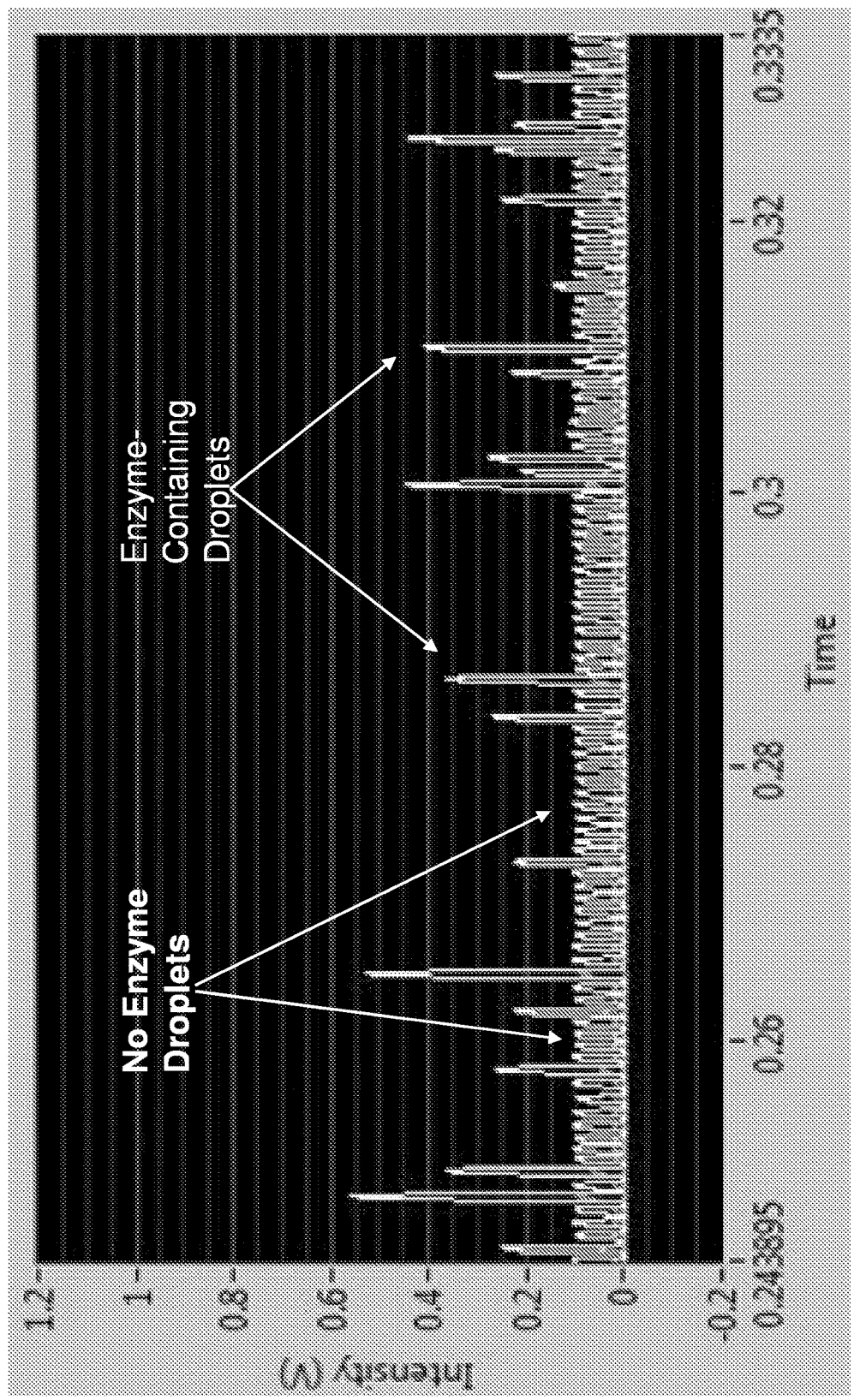
Figure 2B:
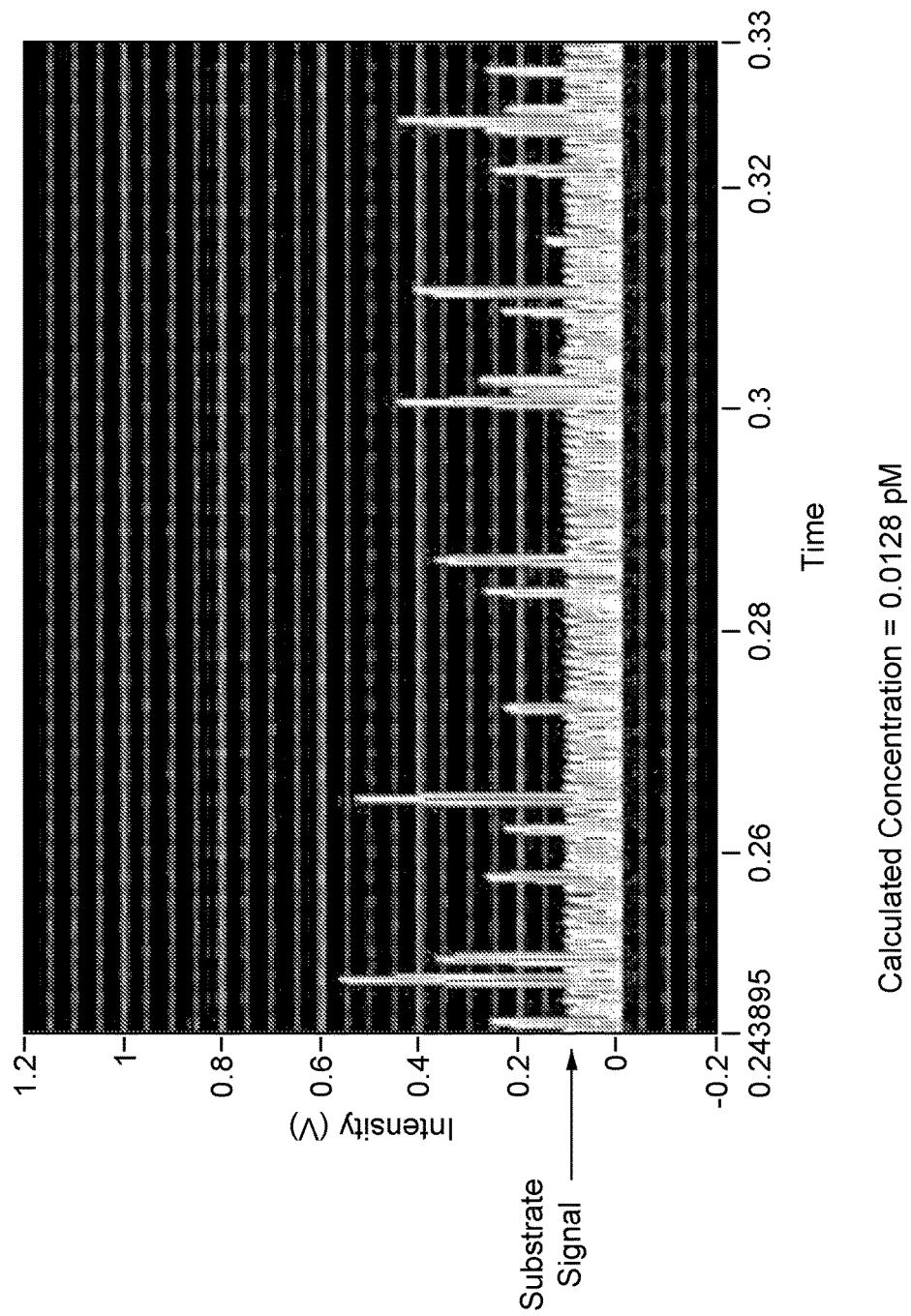
Figure 2D:
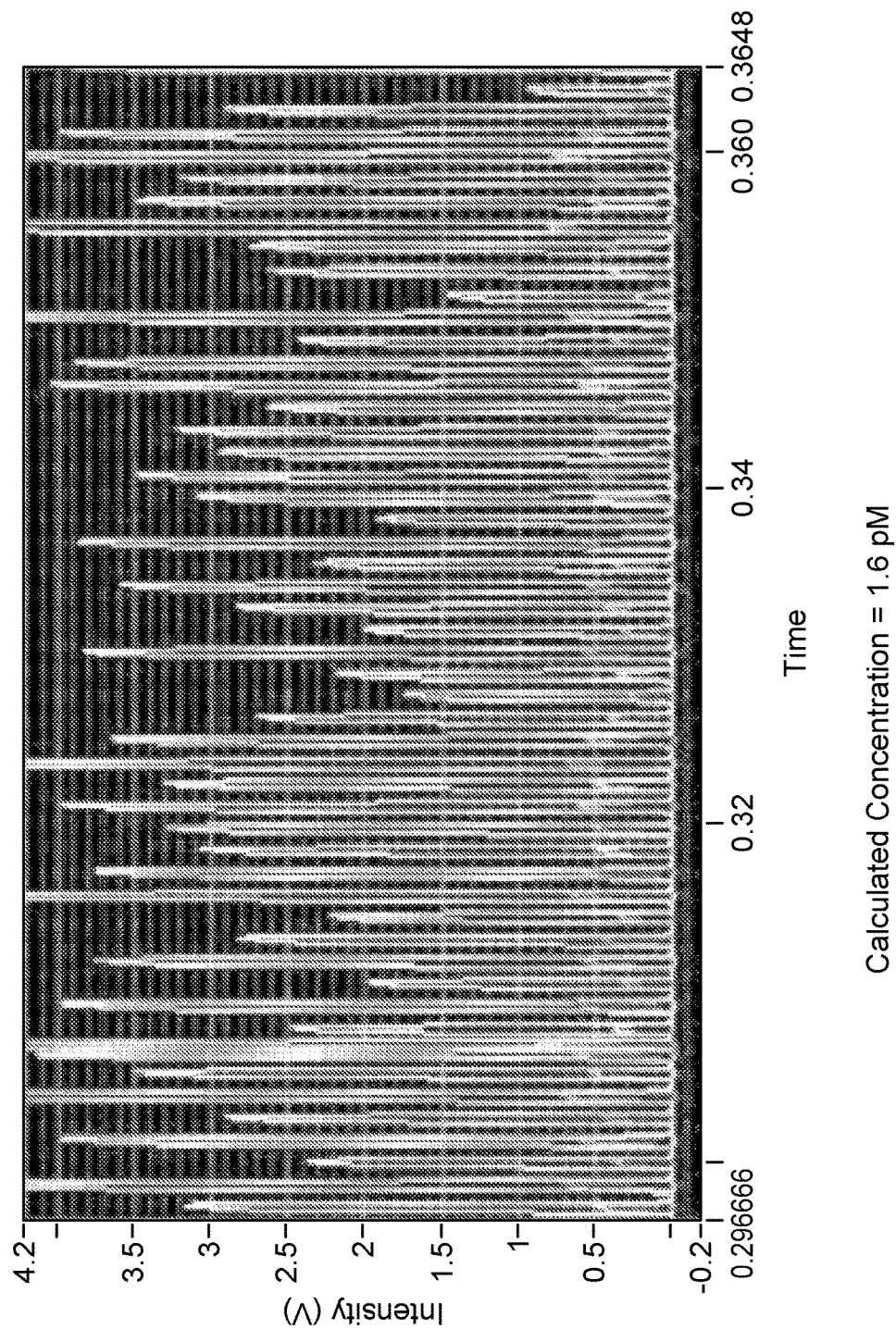

The resulting signal time traces from detection photomultiplier tubes show examples for when either there were no enzyme molecules loaded or after loading enzyme molecules but before incubation (shown in FIG. 1F with an insert showing a zoomed image of 10 individual droplet traces), and droplets generated with a low concentration of enzyme after incubation (FIG. 1G). The droplets that have no enzyme molecules (or have enzyme molecules that were not incubated to allow for enzymatic activity) show uniformly low fluorescent signal intensity, coming from the unconverted fluorogenic substrate. For the case where a low concentration of enzyme was used (see FIG. 1G) loading of enzyme molecules into droplets occurs in a quantized manner, with the signal time trace showing droplets that have no enzyme molecules (with similar signal intensity to that seen at generation) and droplets with enzyme molecules (showing quantized levels of signal intensity that correspond to different numbers of enzyme molecules per droplet).

The distribution of the number of enzyme molecules per droplet (i.e. 0, 1, 2, 3, etc. molecules per droplet) is dependent on the starting concentration of enzyme loaded into the droplets and the whether the enzyme molecules are in un-dissociated complexes. FIGS. 2A-2D and FIGS. 3A-3D illustrate this phenomenon, showing the time traces (FIGS. 2A-2D) and histogram distributions (FIGS. 3A-3D) for increasing concentrations of β-gal, as shown by fluorescent intensity of FITC (lowest concentration shown in FIGS. 2A and 3A, highest concentration shown in FIGS. 2D and 3D). These measurements were made on droplets that had been incubated for about an hour. As the starting enzyme concentration is increased, the time traces show the number of 'negative' (no enzyme) droplets decrease, the number of 'positive' droplets increase, and the number of enzyme molecules in any positive droplet increases (seen as a higher signal intensity).

Figure 3A:
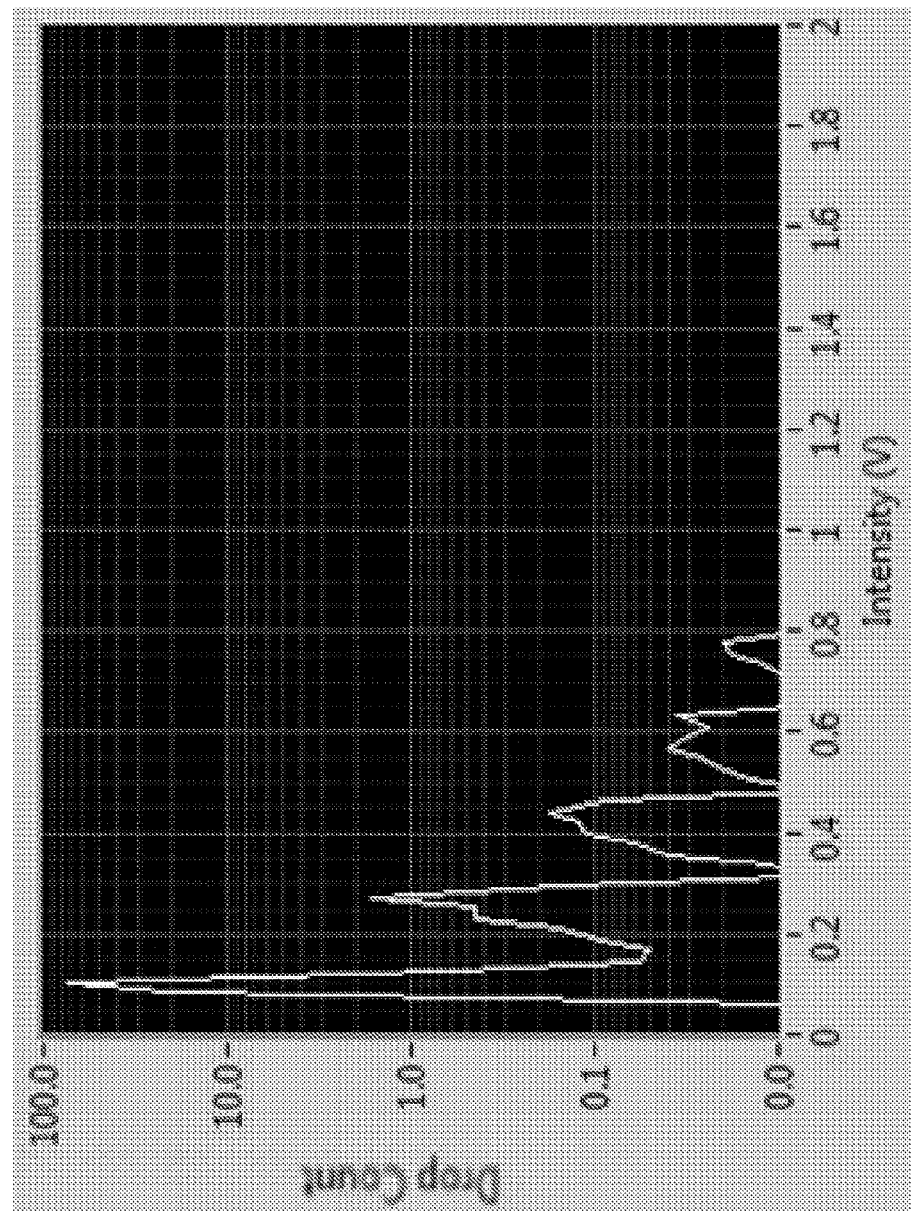
FIGS. 3A-3D show readouts of histograms. Increasing enzyme concentrations shifts the distribution from quantized to average regime.
Figure 3B:
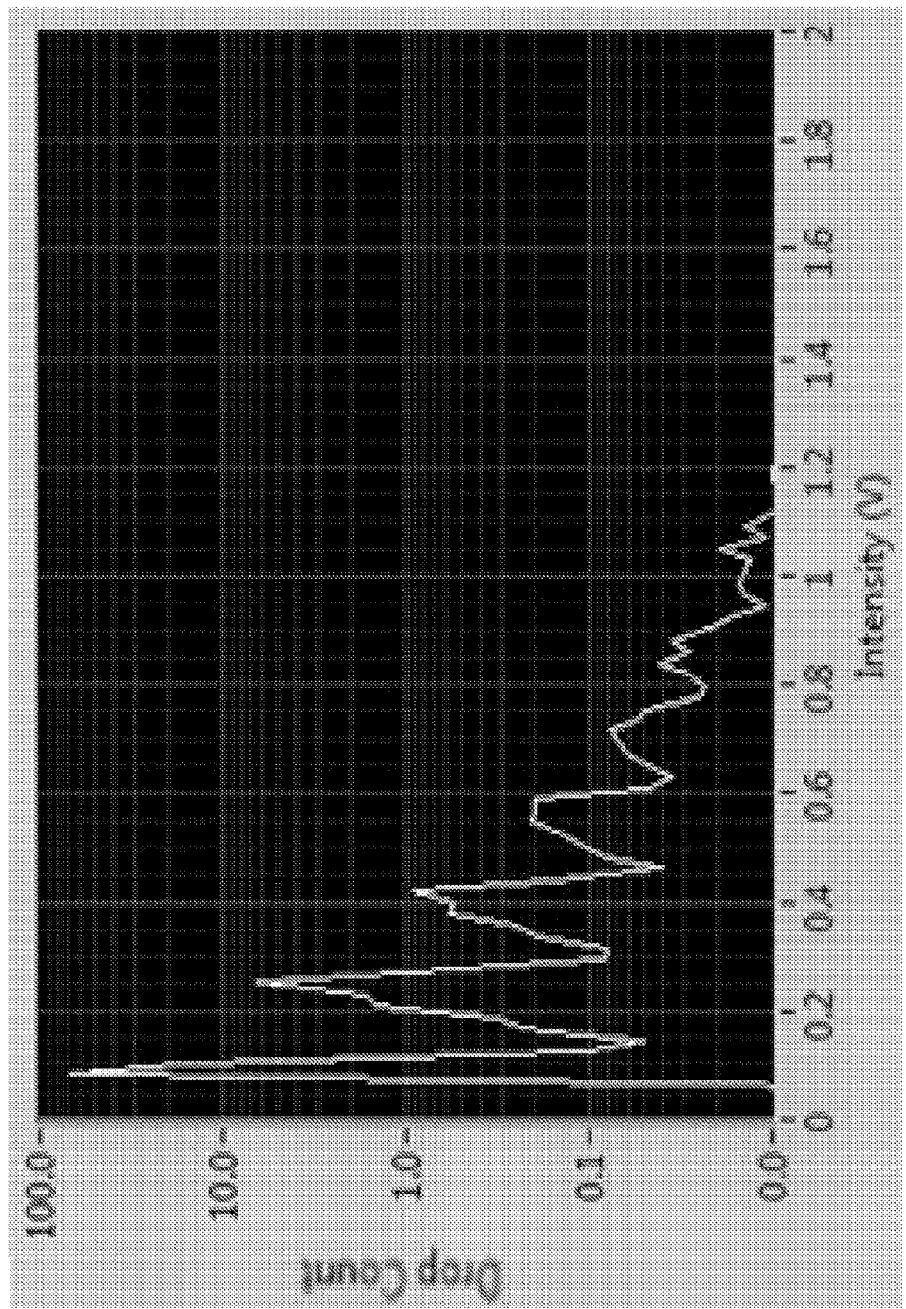
Figure 3C:
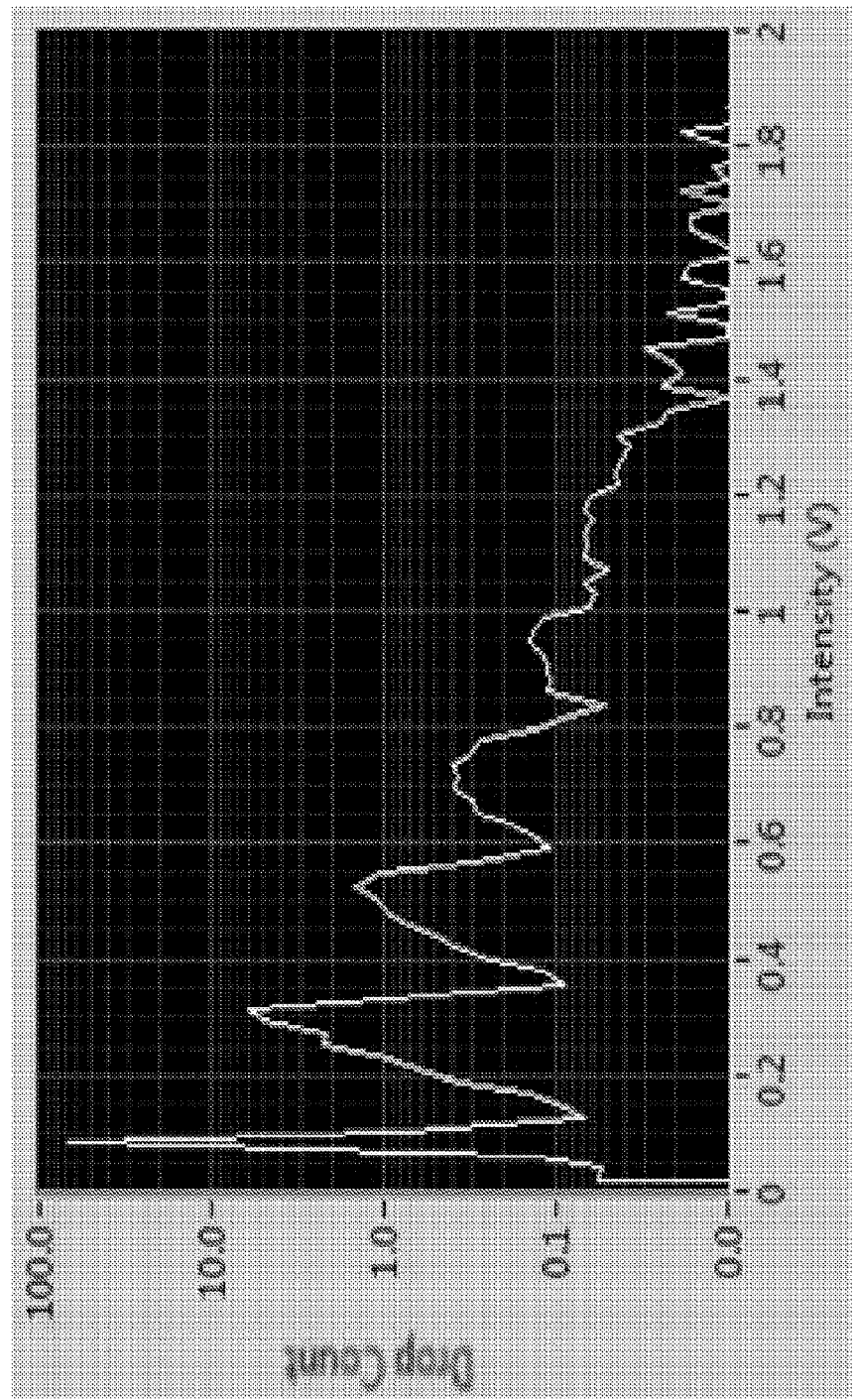
Figure 3D:
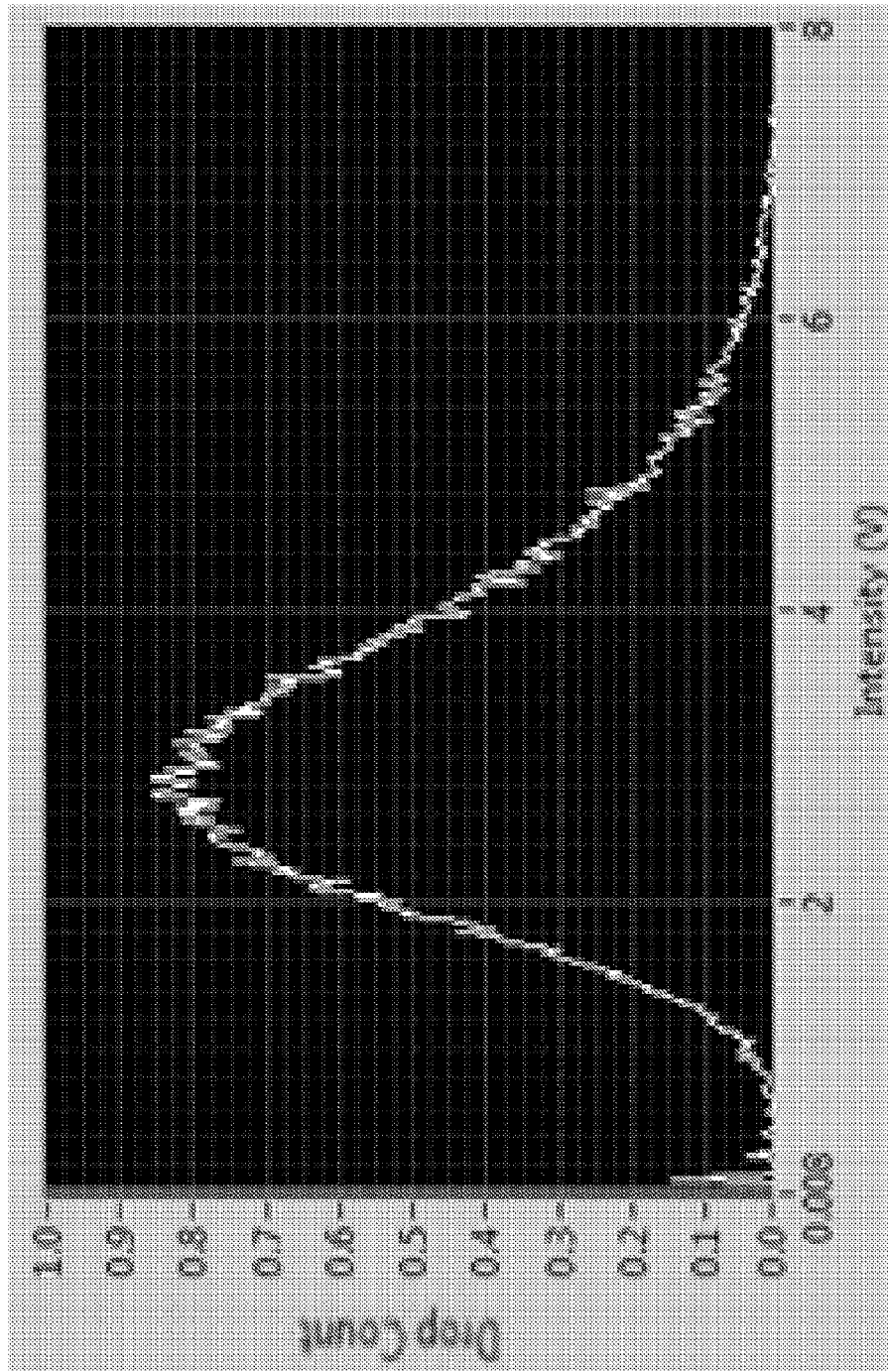

The distribution of enzyme molecules into droplets can occur according to a Poisson Distribution, or can occur in a non-Poisson fashion. FIG. 3A shows a non-Poisson distribution. In some cases the degree to which the distribution varies from a Poisson distribution will be indicative of a degree of aggregation of the component. In some cases the interpretation of the variation from a Poisson distribution will be diagnostic. In FIG. 3A, the x-axis is given in volts indicting reporter intensity as measured through a photomultiplier. An appropriate scaling factor can be used (e.g., determined separately) to convert V to number of molecules per droplet. As shown in FIG. 3A, the first peak at about 0.1 V can indicate that a number of the droplets (i.e., Drop Count) that had no β-gal activity in them. The second peak about 0.23 V can indicate a number of droplets that each had one active unit of enzyme. The third peak about 0.42 V can indicate a number of droplets that each contained two active units of enzyme. The fourth peak, at about 0.58 V, can indicate a number of droplets that contained three units of active enzyme. The fifth peak, at about 0.76 V, can indicate a number of droplets that contained four active units of enzyme. FIGS. 3B-3C show greater concentration of enzyme (i.e., less dilution). In certain embodiments, for an enzyme that exhibits no aggregation or covalent or non-covalent complex formation, a plot at the concentration illustrated in FIG. 3A would show a Poisson distribution. FIG. 3A can indicate that a substantial and statistically significant number of droplets contain more than 1 enzyme unit than is predicted by Poisson. Thus, FIG. 3A can show that β-gal exhibits aggregation. When the starting enzyme concentration is 1.6 pM (FIGS. 2D and 3D, there are no negative droplets, and the histogram shows most droplet signals centered around a single mean value, with a much smaller number showing a quantized distribution like that seen at lower concentrations (several small peaks close to the origin).

Figure 4A:
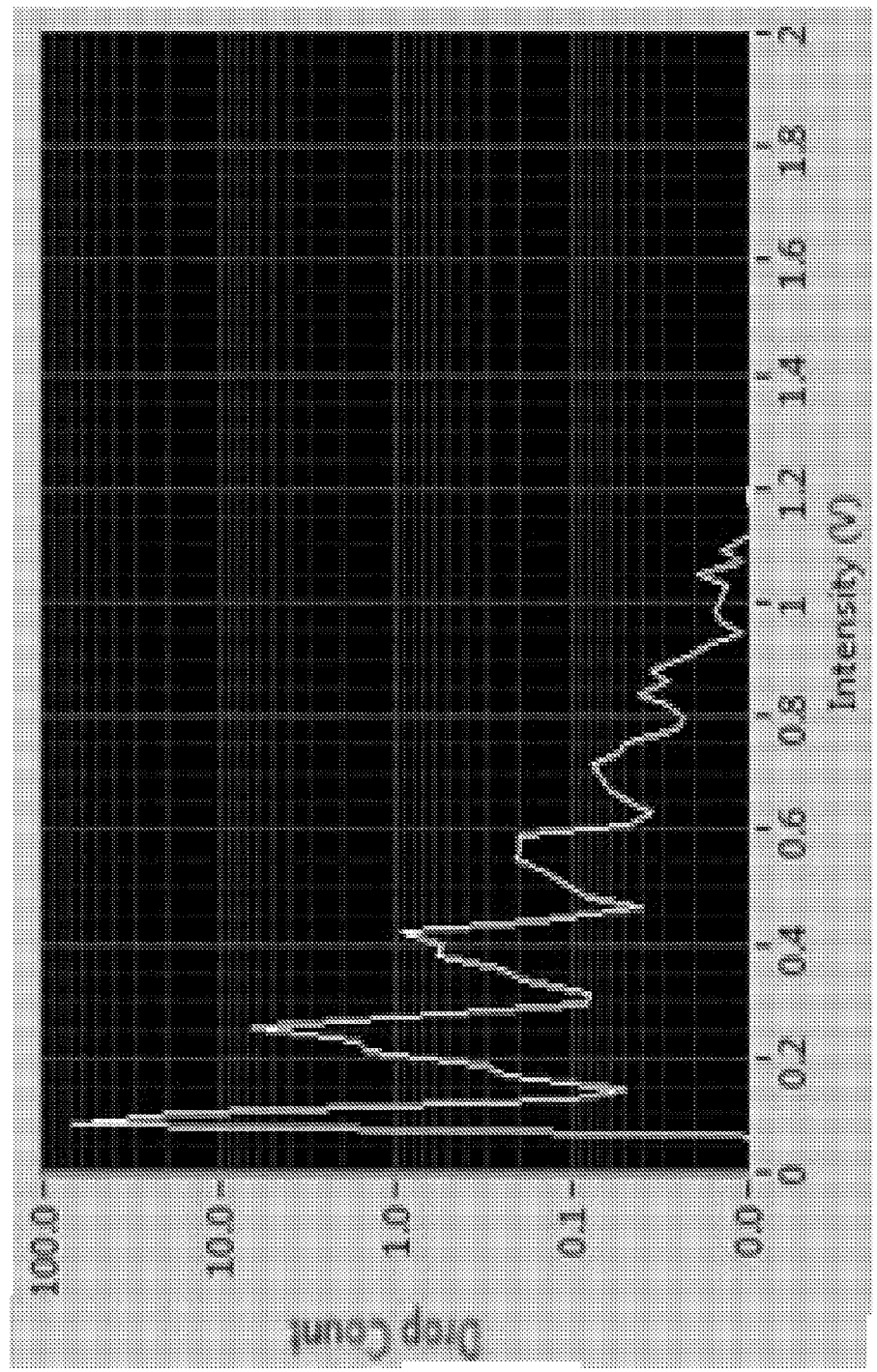
FIGS. 4A and 4B illustrate concentration determination using digital droplet data. Digital counting measurement of enzyme concentration matches known starting amount.
Figure 4B:
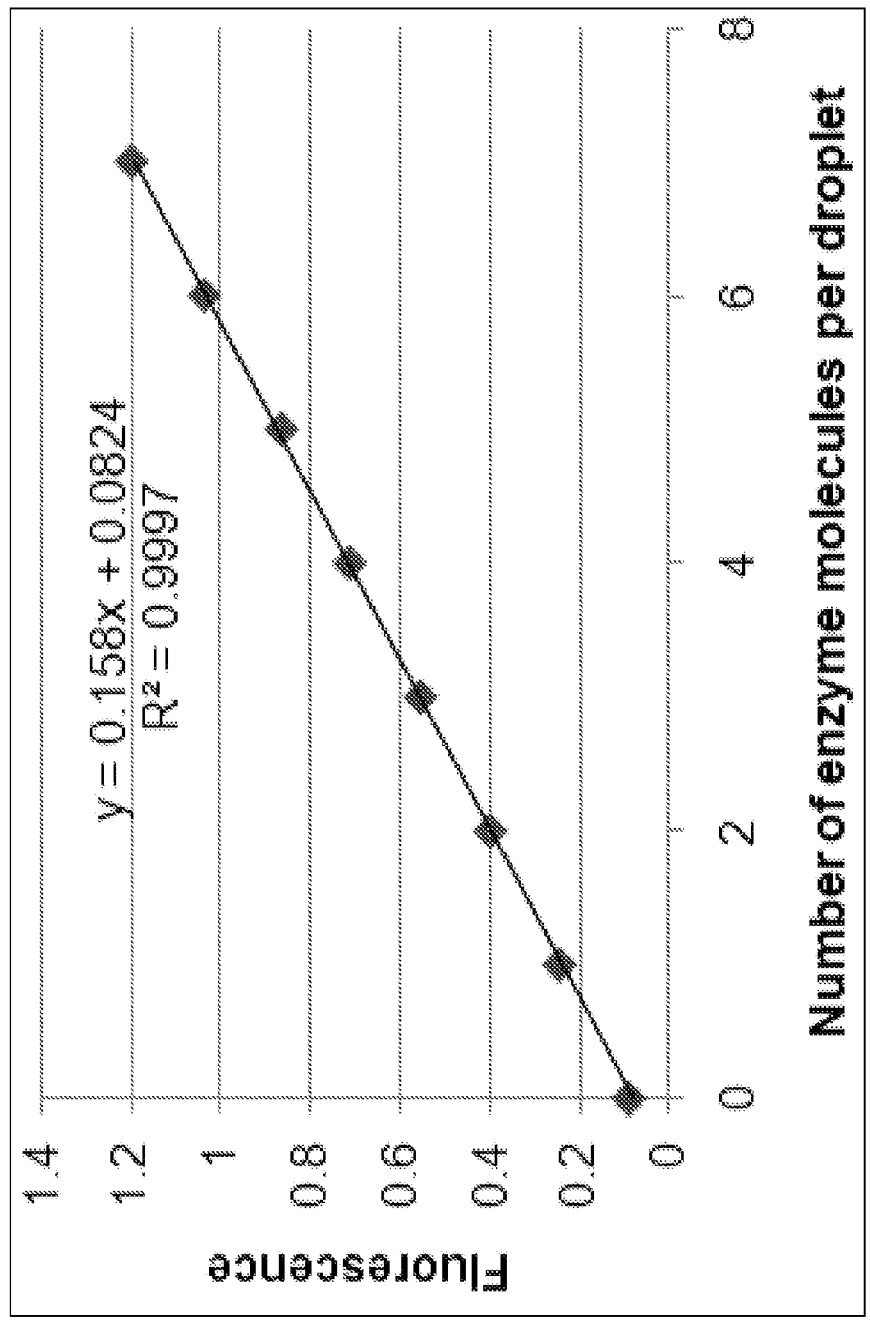

FIGS. 4A and 4B show an example of how this data can be used to quantify the concentration of active enzyme molecules loaded into droplets. FIG. 4A shows a readout histogram from an enzyme concentration that was calculated to be 0.0128 pM. Using the histogram from an enzyme concentration calculated to be 0.0128 pM, based on multiplying the starting concentration and the dilution factor (FIG. 4A), each peak's mean is determined and plotted as a function of integer enzyme molecules to show linearity (FIG. 4B). The number of droplets within each peak and the number of active enzyme molecules within each peak are counted and tabulated. The results are listed in Table 1.

TABLE 1

Distribution of #Droplets with #Molecules

| Enzyme/droplet | Droplets | #enzymes |
| --- | --- | --- |
| 0 | 113458 | 0 |
| 1 | 15249 | 15249 |
| 2 | 3637 | 7274 |
| 3 | 1356 | 4068 |
| 4 | 536 | 2144 |
| 5 | 280 | 1400 |
| 6 | 139 | 834 |
| 7 | 73 | 511 |
| >7 | 138 | 1405 |
| Total: | 137866 | 32885 |

By dividing the totals from Table 1 (number of active enzyme molecules over total number of droplets counted) a number of molecules per droplet can be calculated as shown in Equation 1.

$$(\#molecules/droplet) = (32885/134866) = 0.24 \quad (1)$$

By multiplying by the appropriate scaling factors, the measured concentration (MC) can be calculated using Equation 2:

$$MC(pM) = \frac{\#molecules}{droplet} \times \frac{droplet}{volume(pL)} \times \frac{1.0\,pM}{0.6023\,molecules/pL} \quad (2)$$

Using the value given by Equation 1 in Equation 2, gives the result shown in Equation 3.

$$MC(pM) = \frac{0.24\,molecules}{droplet} \times \frac{droplet}{30\,pL} \times \frac{1.0\,pM}{0.6023\,molecules/pL} \quad (3)$$
$$= 0.01275\,pM$$

For this example, the measured concentration was 0.01275 pM, with the expected concentration based on dilution factor being 0.0128 pM.

The dynamic range of the assay can span regimes where the number of enzyme molecules is discretely quantized in all droplets or where the majority of droplets (or all droplets) contain a mean (with a distribution around the mean) number of enzyme molecules. For the specific format described in the example (i.e. droplet size, enzyme and substrate used) typically enzyme concentrations greater than ~pM can be analyzed using the mean distribution (and also the small quantized tail seen near the origin of the graph shown in FIG. 3D) and enzyme concentrations lower than ~pM can be analyzed using digital counting of the total number of droplets, the number of enzyme-containing droplets, and using the quantized signals from enzyme-containing droplets to count the number of enzyme molecules per droplet. Thus, the dynamic range of the assay is extremely wide, with the lower limit of detection determined by the number of detectable molecules present in the sample and the length of time required to run a sufficient number of droplets through the detector (e.g. if the droplet system runs at $10^6$ droplets per hour, the limit of detection is 1 in $10^6$ in an hour, and the limit of detection is 1 in $10^7$ in 10 hours), and the upper limit determined by the amount of substrate converted to product (as enzyme concentrations get higher, the substrate concentration will have to increase in order for the product fluorescence to remain linearly (or correlatively) related to enzyme mean concentration). Additional parameters that can be adjusted include the time and temperature of incubation, as well as the droplet volume used, and additional reaction components. In certain embodiments, fluid partitions are droplets and assays are performed in systems in which droplets are run past a detector at 3,000 s. In some embodiments, droplets are run at 10,000/s or at about 100,000 per second. In some embodiments, a lower limit of detection is 1 in $10^9$ and a flow rate is $10^9$ per hour.

FIG. 5 shows an illustration of the concept and workflow for a digital droplet ELISA assay, one example of an upfront assay that can be coupled to the digital reporter enzyme assay readout. When protein concentrations are too low for standard detection methods (typically low-sub-picomolar), this invention enables protein quantification by counting individual protein molecules with a fluorescent readout. Droplets containing a single molecule (e.g. in an ELISA sandwich) will be fluorescent, and the number of fluorescent droplets in a population of total droplets will yield a digital count of molecules per volume (i.e. concentration) down to a limit of detection dependent only on the number of droplets examined.

FIG. 5 shows one example ELISA assay format and should not be considered the only or preferred format (e.g. magnetic beads could be added following antibody binding in solution). The protein-containing sample (three proteins shown as diamonds with the rare target protein to be counted shown as solid diamonds) is combined with the binding reagents and incubated for a sufficient time to bind into productive complexes.

In the "ELISA Sandwich Formation" step, each target protein molecule is bound to two affinity reagents (each binding separate epitopes of the same target molecule), generating an immunoaffinity "sandwich" complex. In the example shown, one of the affinity reagents (e.g. antibody) is immobilized onto a magnetic bead while the other biotinylated antibody is free in solution. In certain embodiments, the number of magnetic beads (with immobilized antibody) is significantly greater than the number of target proteins in solution, so that single target proteins are bound by single beads. If the second antibody is used at the same time, its concentration should be greater than the number of target molecules, but less than the number of immobilized antibodies. Alternatively, the second antibody can be added following the first binding step (ensuring that all target molecules are bound to the immobilized antibody first).

After the target proteins are bound into sandwich complexes, the magnetic beads are retained by a magnetic field to allow removal of unbound non-target proteins and free antibodies, and washed to remove non-specific binders.

Addition of the reporter enzyme (e.g. streptavidin-beta galactosidase) results in binding to the second biotinylated antibody and assembly of the final ELISA sandwich, which is again washed to remove unbound reporter enzyme. The final material (see, e.g., FIG. 6A) is re-suspended in a small volume, along with a fluorogenic substrate, for processing in the digital droplet readout.

Figure 6B:
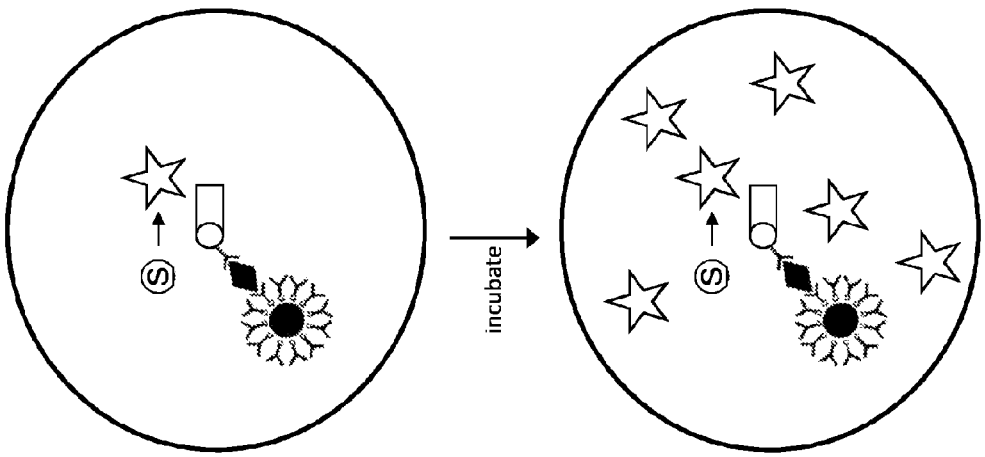
FIGS. 6A-6D illustrates different digital droplet ELISA readout counting modes.
Figure 6A:
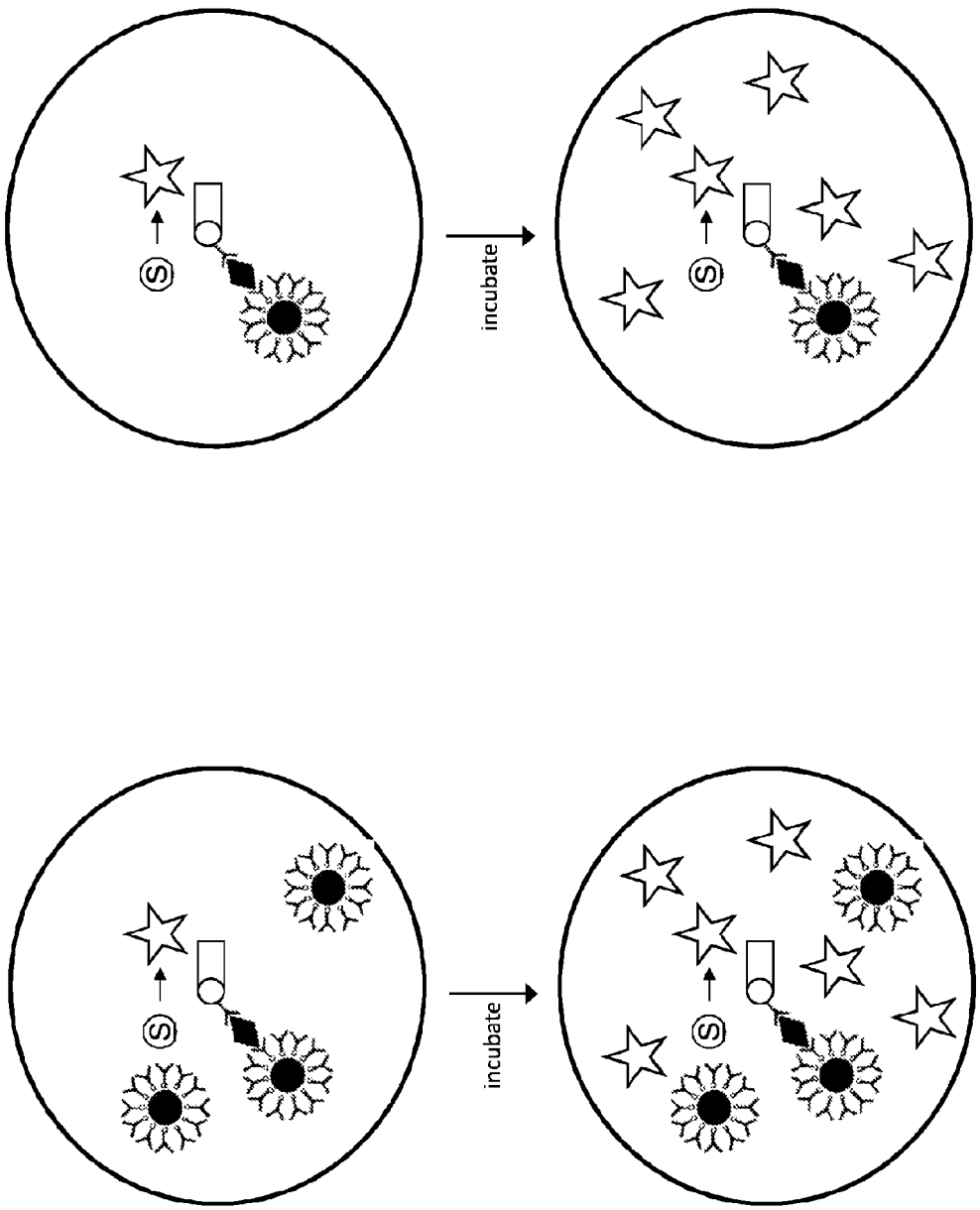

FIGS. 6A-6D show a number of different readout 'modes' for running the digital droplet readout, following the ELISA sandwich complex construction. In FIG. 6A, more than one magnetic bead is in each generated droplet, but only a single ELISA sandwich is in any single droplet (e.g. in this case sub-micron magnetic beads are used).

FIG. 6B shows a mode where at most a single bead is in each droplet, with at most one ELISA sandwich.

Figure 6D:
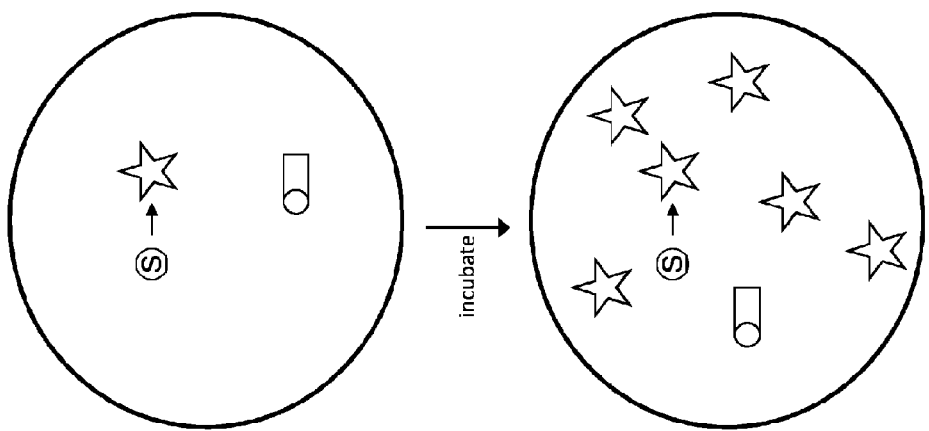
Figure 6C:
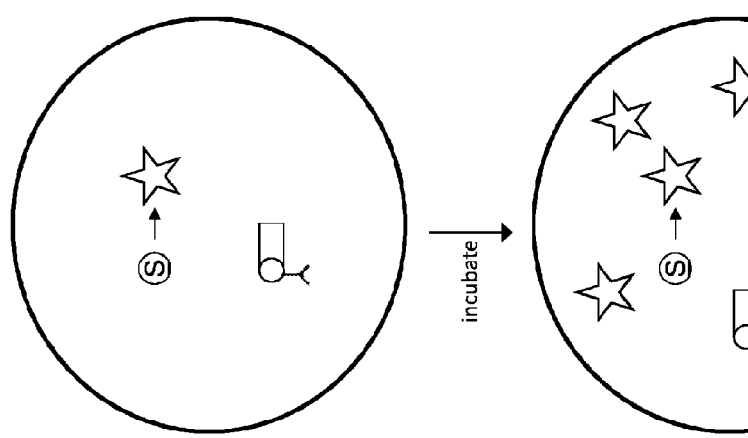

FIG. 6C shows a mode where the second antibody complexed to the reporter enzyme has been eluted off of the magnetic bead, and the droplets are loaded such that at most one antibody-reporter complex is present in any droplet.

In FIG. 6D, the reporter enzyme itself is released off of the magnetic bead, with droplets loaded such that at most one enzyme molecule is present in any droplet.

Any suitable method can be used for releasing the enzyme from the ELISA sandwich. Exemplary methods include: 1) competition of a desthiobiotin-streptavidin interaction using biotin; 2) reduction of a linker that contains a disulfide bond; 3) enzymatic cleavage of a linker group. Other variations can be considered, and Poisson and non-Poisson models can be used to enable high occupancy loading while still providing quantitative counting.

Figure 7A:
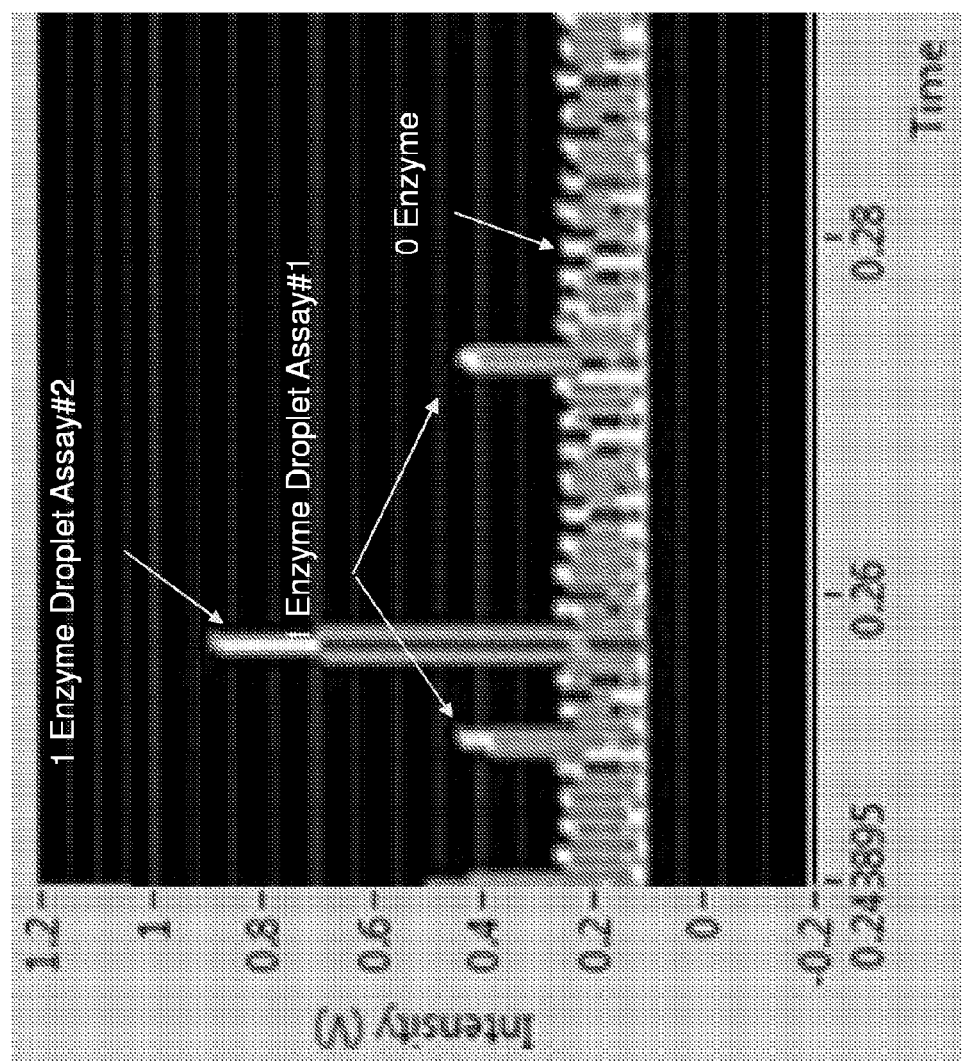
FIGS. 7A and 7B show embodiments for multiplexing digital assay.
Figure 7B:
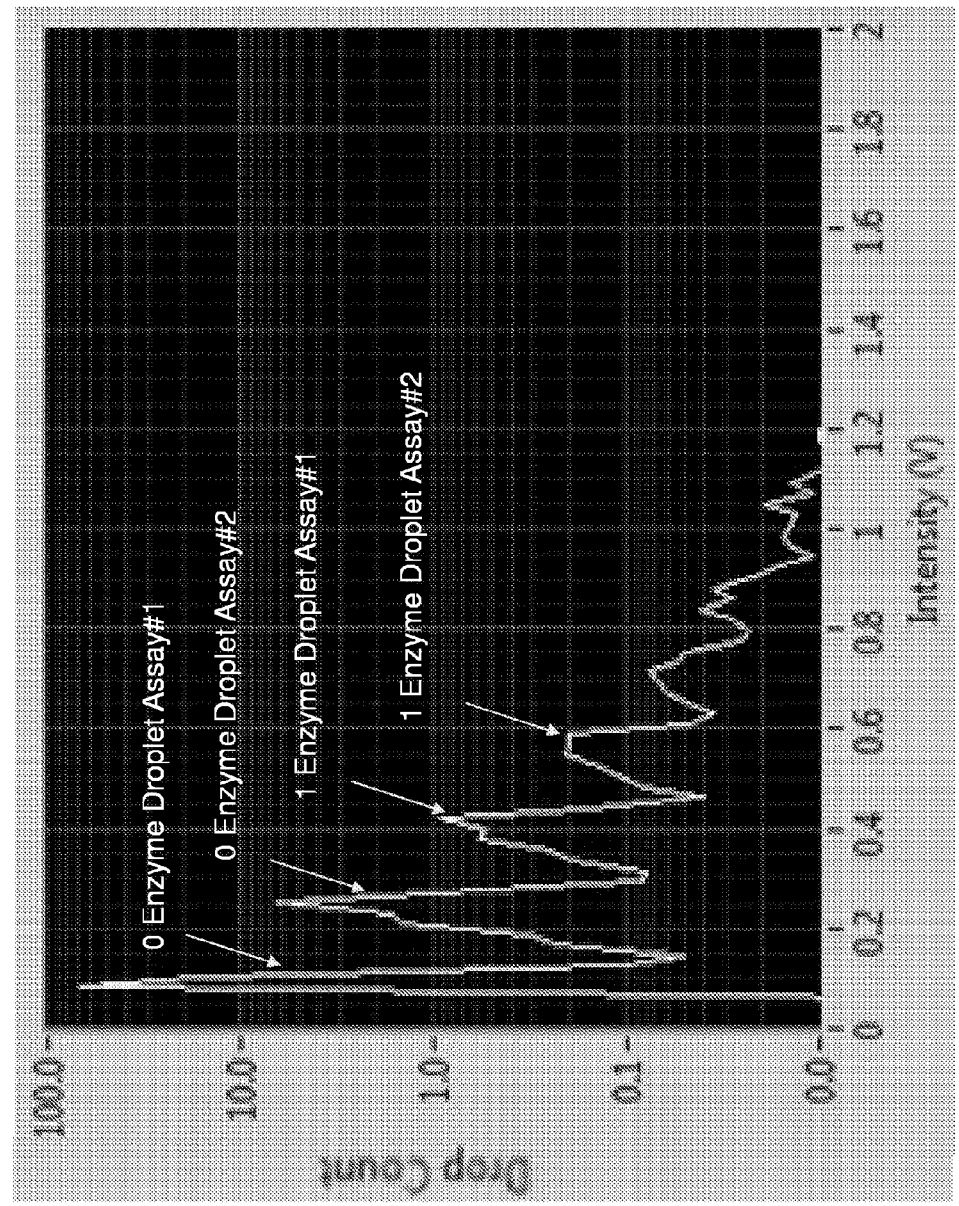

With reference to FIGS. 7A and 7B, the invention provides methods for multiplexing digital droplet reporter enzyme readout. Several modes for multiplexing a digital assay are provided.

In certain embodiments, methods including generating droplets that contain different fluorogenic substrates and enzymes that produce different fluorescent products. For example, beta galactosidase and FDG produce FITC, whereas horseradish peroxidase and Amplex Red produce resorufin. The first method uses completely separate enzyme and fluorogenic substrate pairs loaded into droplets at the same time. For example, beta galactosidase and FDG (FITC is the fluorescent product, with a peak emission wavelength of 518 nm) can be used to count one set of target molecules, while horseradish peroxidase and Amplex Red (Resorufin is the fluorescent product, with a peak emission wavelength of 582 nm) can be used to simultaneously report on a second set of target molecules, as the detection wavelengths can be easily distinguished with standard laser/filter setups.

Some combinations of different reporter enzymes and different substrates producing the same fluorescent product can be used. For example, beta galactosidase catalyzes reactions of FDG while alkaline phosphatase catalyzes reactions of FDP, with each of these combinations producing the same fluorescent product (FITC). Nonetheless, the endpoint product concentration for each single enzyme can be discriminated when multiplexing.

FIG. 7A illustrates discrimination by signal strength at endpoint. While different enzymes and substrates are used, the substrates generate the same fluorescent product (e.g. FITC). Careful titration of the endpoint product concentrations can enable separate counting of each target (e.g., traces with distinct intensities in FIG. 7A).

FIG. 7B illustrates discrimination by running at different time points. In these embodiments, a kinetic assay can be used rather than an endpoint assay (e.g. alkaline phosphatase and fluorescein diphosphate yield FITC as a product with much faster kinetics than beta galactosidase and FDG). One assay (assay#1) runs for a period of time and produces a detectable product. After an amount of time, the detectable product hits a plateau in intensity. Assay #1 is multiplexed with (i.e., run simultaneously with) assay #2. Assay #2 proceeds more slowly than assay #1. By the time that assay #2 begins any substantially uptick in activity, the product of assay #1 has plateaued. Thus, the level of detectable product from the plateau of assay #1 provides a baseline for the level of product of assay #2. Such a pattern can be further multiplexed to any suitable level of plexity.

In certain embodiments, all droplets within an assay have a substantially identical size (e.g., even where optical labeling is used). The same nozzle 105 can be used to generate droplets of identical size (discussed in greater detail below). Further, since all droplets are labeled separately for multiplexing, the droplets can be incubated identically, due to the fact that they can be handled in the same chamber or apparatus. Similarly, all droplets can be read with the same optical mechanism (e.g., they all flow through the same channel past the same detection point on-chip). Thus, optical sample indexing allows for higher throughput and better data comparisons.

While some descriptions herein illustrate digital enzyme quantification in droplets, systems and methods of the invention are applicable to any suitable fluid partition. Fluid volumes for partitions can be provided by chambers made from closing valves, SLIP-chips, wells, spontaneous breakup to form droplets on a structured surface, droplets formed using electrowetting methods, etc.

Fluorescence Polarization/Fluorescence Lifetime

As described herein, the biological/chemical entity to be analyzed may itself be detectable, for example by a characteristic fluorescence, or it may be labeled or associated with a reporter that produces a detectable signal when the desired protein is present, or is present in at least a threshold amount.

Luminescent colloidal semiconductor nanocrystals called quantum dots or q-dots (QD) are inorganic fluorophores that have the potential to circumvent some of the functional limitations encountered by organic dyes. In particular, CdSe—ZnS core-shell QDs exhibit size-dependent tunable photoluminescence (PL) with narrow emission bandwidths (FWHM ~30 to 45 nm) that span the visible spectrum and broad absorption bands. These allow simultaneous excitation of several particle sizes (colors) at a common wavelength. This, in turn, allows simultaneous resolution of several colors using standard instrumentation. CdSe—ZnS QDs also have high quantum yields, are resistant to photodegradation, and can be detected optically at concentrations comparable to organic dyes.

Quantum dots are nano-scale semiconductors typically consisting of materials such as crystalline cadmium selenide. The term 'q-dot' emphasizes the quantum confinement effect of these materials, and typically refers to fluorescent nanocrystals in the quantum confined size range. Quantum confinement refers to the light emission from bulk (macroscopic) semiconductors such as LEDs which results from exciting the semiconductor either electrically or by shining light on it, creating electron-hole pairs which, when they recombine, emit light. The energy, and therefore the wavelength, of the emitted light is governed by the composition of the semiconductor material. If, however, the physical size of the semiconductor is considerably reduced to be much smaller than the natural radius of the electron-hole pair (Bohr radius), additional energy is required to "confine" this excitation within the nanoscopic semiconductor structure leading to a shift in the emission to shorter wavelengths. Three different q-dots in several concentrations each can be placed in a microdroplet, and can then be used with a microfluidic device to decode what is in the drop. The Q-dot readout extension to the fluorescence station can be incorporated into the design of the microfluidic device. A series of dichroic beamsplitters, emission filters, and detectors can be stacked onto the system, allowing measurement of the required five emission channels (two fluorescence polarization signals and three q-dot bands).

Fluorescence Polarization (FP) detection technology enables homogeneous assays suitable for high throughput screening assays in the Drug Discovery field. The most common label in the assays is fluorescein. In FP-assay the fluorophore is excited with polarized light. Only fluorophores parallel to the light absorb and are excited. The excited state has a lifetime before the light emission occurs. During this time the labeled fluorophore molecule rotates and the polarization of the light emitted differs from the excitation plane. To evaluate the polarization two measurements are needed: the first using a polarized emission filter parallel to the excitation filter (S-plane) and the second with a polarized emission filter perpendicular to the excitation filter (P-plane). The Fluorescence Polarization response is given as mP (milli-Polarization level) and is obtained from the equation:

$$\text{Polarization (mP)} = 1000*(S-G*P)/(S+G*P)$$

Where S and P are background subtracted fluorescence count rates and G (grating) is an instrument and assay dependent factor.

The rotational speed of a molecule is dependent on the size of the molecule, temperature and viscosity of the solution. Fluorescein has a fluorescence lifetime suitable for the rotation speeds of molecules in bio-affinity assays like receptor-ligand binding assays or immunoassays of haptens. The basic principle is that the labeled compound is small and rotates rapidly (low polarization). When the labeled compound binds to the larger molecule, its rotation slows down considerably (polarization changes from low to high polarization). Thus, FP provides a direct readout of the extent of tracer binding to protein, nucleic acids, and other biopolymers.

Fluorescence polarization technology has been used in basic research and commercial diagnostic assays for many decades, but has begun to be widely used in drug discovery only in the past six years. Originally, FP assays for drug discovery were developed for single-tube analytical instruments, but the technology was rapidly converted to high-throughput screening assays when commercial plate readers with equivalent sensitivity became available. These assays include such well-known pharmaceutical targets such as kinases, phosphatases, proteases, G-protein coupled receptors, and nuclear receptors. Other homogeneous technologies based on fluorescence intensity have been developed. These include energy transfer, quenching, and enhancement assays. FP offers several advantages over these. The assays are usually easier to construct, since the tracers do not have to respond to binding by intensity changes. In addition, only one tracer is required and crude receptor preparations may be utilized. Furthermore, since FP is independent of intensity, it is relatively immune to colored solutions and cloudy suspensions. FP offers several advantages in the area of instrumentation. Because FP is a fundamental property of the molecule, and the reagents are stable, little or no standardization is required. FP is relatively insensitive to drift in detector gain settings and laser power.

The dyes chosen for FP are commonly used in most cell- and enzyme-based assays and are designed not to overlap significantly with the q-dots. The dyes are evaluated both independently and together with the q-dots (at first off-instrument) to assess the cross-talk. Preferably, the liquid q-dot labels are read outside a spectral wavelength band currently used in FACS analysis and sorting (i.e., the dyes flourescein, Cy3, Cy5, etc). This permits the use of currently-available assays (dependent on these dyes). Using specific q-dots, crosstalk is minimized.

Accordingly, the present invention provides methods to label droplets and/or nanoreactors formed on a microfluidic device by using only a single dye code to avoid cross-talk with other dyes during FP. Additionally, the present invention provides methods to create FP dye codes to label compounds contained within liquids (including droplets and/or nanoreactors) where the compound is designed to be differentiated by FP on a microfluidic device. In this manner, dye codes having the same color, absorption, and emission could be used to label compounds within liquids.

In one aspect, the present invention is directed to the use of fluorescence polarization to label liquids. Droplets can be labeled using several means. These labeling means include, but are not limited to, the use of different dyes, quantum dots, capacitance, opacity, light scattering, fluorescence intensity (FI), fluorescence lifetime (FL), fluorescence polarization (FP), circular dichroism (CD), fluorescence correlation and combinations of all of these previous labeling means. The following disclosure describes the use of FP and FI as a means to label droplets on a microfluidic device. In addition, the use of FL as a means to adjust the overall FP of a solution, and by varying the concentration of the total FI, to create a 2-dimensional encoding scheme is demonstrated.

In general, molecules that take up more volume will tumble slower than a smaller molecule coupled to the same fluorophore. FP is independent of the concentration of the dye; liquids can have vastly different concentrations of FITC in them yet still have identical FP measurements.

In a preferred embodiment, a FP dye is an organic dye that does not interfere with the assay dye is used. Furthermore, since the total intensity of the FP dye can be quantified, a second dimension in which to label the droplet is provided. Thus, one can exploit the differences in FP to create an encoding scheme of dye within a liquid solution, including droplets. Examples of ways to exploit the differences in FP are described in WO 2007/081385 and WO 2008/063227. In a single dimension, FP can be used to create an encoding scheme. However, the present invention can also use Fluorescence Intensity (FI) of the overall solution to create even more labels in a second dimension. Interestingly, the differences of the fluorescence lifetime (FL) of two dyes with spectral overlap in the detected emission wavelength to change the overall FP of the combined solution can also be exploited.

Although the use of multiple compounds to which a dye molecule is attached to span a range of FP can be utilized, it is also possible to span the range using a high and low molecular weight compound set. For example, a dye can be attached to a large compound (for example streptavidin) and kept at a fixed concentration, to which a smaller compound (for example, a free dye molecule) would be titrated into the same solution. The FP of the solution can be adjusted to be in discernable increments from the value of the large molecule to somewhere slightly greater than the FP of the smaller molecule. The [total] dye intensity can be varied by varying the concentration of the mixture of the two dye-attached compounds. By varying total dye concentration and the FP, two dimensions can be used to generate the FP dye codes (FPcodes). Accordingly, many FPcodes can be generated using only two compounds.

In some embodiments, fluorescent polarization is used for digital assays. In this method, positive (enzyme-containing) droplets are identified and counted using changes in the fluorescence polarization of fluorescent molecules in the droplets. Fluorescence polarization (FP) detection technology can use a label such as fluorescein. In an FP-assay the fluorophore is excited with polarized light. Only fluorophores parallel to the light absorb and are excited. The excited state has a lifetime before the light emission occurs. During this time the labeled fluorophore molecule rotates and the polarization of the light emitted differs from the excitation plane. In some embodiments, to evaluate the polarization two measurements are used: the first using a polarized emission filter parallel to the excitation filter (S-plane) and the second with a polarized emission filter perpendicular to the excitation filter (P-plane). Fluorescence Lifetime (FL) changes can be detected based on the chemical environment of the fluorophore such that bound and unbound antibodies can be distinguished by FL measurements well known to one skilled in the art.

The rotational speed of a molecule is dependent on the size of the molecule, temperature and viscosity of the solution. The principle here is that the labeled compound is small and rotates rapidly (low polarization). When the labeled compound binds to the larger molecule, its rotation slows down considerably (polarization changes from low to high polarization). In general, molecules that take up more volume will tumble slower than a smaller molecule coupled to the same fluorophore. FP is independent of the concentration of the dye; liquids can have vastly different concentrations of FITC in them yet still have identical FP measurements. Thus, FP provides a direct readout of the extent of binding to protein, nucleic acids, and other biopolymers or targets.

FP offers advantages in the context of multiplexing (discussed in more detail elsewhere herein). Since FP is independent of intensity, it is relatively immune to colored solutions and cloudy suspensions. FP offers several advantages in the area of instrumentation. Because FP is a fundamental property of the molecule, and the reagents are stable, little or no standardization is required.

The dyes chosen for FP include any suitable dye such as, for example, fluorescein, Cy3, Cy5, etc. Suitable dyes include (name followed by [excitation wavelength, emission wavelength]): Cyan 500 [450, 500]; SYBR Green, FAM [483, 533], HEX, VIC [523, 568]; RED 610 [558, 610]; RED 640 [615, 640]; and CY5 [650, 670].

In some embodiments, an FP dye is an organic dye that does not interfere with other labels or dyes in an assay. Furthermore, since the total intensity of the FP dye can be quantified, a second dimension in which to label the partition is provided. Thus, one can exploit the differences in FP to create an encoding scheme of dye within a liquid solution, including droplets. Examples of ways to exploit the differences in FP are described in WO 2007/081385 and WO 2008/063227. Fluorescence polarization is discussed in U.S. Pub. 2010/0022414, the contents of which are hereby incorporated by reference in their entirety.

In the example shown in FIG. 8A, the enzyme Src kinase (Src) phosphorylates a Src substrate peptide and creates a binding surface for a fluorescent reporter. A reporter construct containing the Src homology 2 domain (SH2) and a fluorescein isothiocyanate (FITC) serves as a fluorescent reporter (SH2-FITC). When SH2-FITC is added, it will bind to the phosphorylated Src substrate peptide. FIG. 8B shows the same sequence of steps but in which Src substrate peptide is bound to a bead.

When the fluorescent reporter SH2-FITC is free in solution it has a low fluorescence polarization, whereas when bound to a phosphorylated peptide (e.g., the last step shown in each of FIGS. 8A and 8B) it has a measurably higher fluorescence polarization. Detection of fluorescent polarization indicates a reaction-positive fluid partition. Many other enzymes, binding motifs, and fluorescent reporters can be used.

Allele-Specific Assay

FIG. 10 shows an illustration of the concept and workflow for a digital droplet competitive allele specific enzyme hybridization (CASE) assay, another example of an upfront assay that can be coupled to the digital reporter assay readout. The CASE hybridization assay uses allele-specific oligonucleotide probe hybridization to select rare genomic targets for binding to the reporter enzyme and subsequent digital counting.

Two probe types are used. Wild-type probe 130 is complimentary to the abundant wild-type allele. Wild type probe 130 includes a minor groove binding motif 134 (either 5' or 3' to the targeting oligonucleotide).

Mutant probe 131 is complimentary to the rare mutant allele. Mutant probe 131 includes an immunoaffinity tag 135 (e.g., TAG) on one end and a biotin on the other end. Other binding motifs can be used, but in this example a DIG TAG (which can be bound by an anti-DIG antibody) and biotin (which can be bound by streptavidin) are used.

Wild-type probe 130 with minor groove binder 134 outcompetes any non-specific binding of mutant probe 131 to the wild-type sample DNA, thus limiting hybridization and duplex formation such that only two duplex species form: wild-type DNA hybridized to wild-type probe 130, and mutant DNA hybridized to mutant probe 131. An excess of the two probes over sample DNA is used, ensuring that each single strand of mutant sample DNA is in a duplex with one mutant allele probe.

Following duplex formation, a single-strand nuclease is added such as S1 nuclease. The nuclease digests any unbound mutant probe 131 such that tag 135 is dissociated from the biotin.

Magnetic beads coupled to anti-TAG antibodies are next added in excess, such that each bead will bind at most one complex of probe 131 and tag 135. The beads are immobilized using magnet 137 and washed to remove non-specifically bound material (digested biotinylated probe and the single strand nuclease).

Streptavidin-coupled reporter enzyme 139 is next added. After washing, the only enzyme remaining immobilized on the magnet is present in a one-to-one stoichiometry with the original rare mutant allele present in the sample DNA. Finally, the reporter enzyme is counted using the digital droplet reporter enzyme assay, as above.

While shown in FIG. 10 in a certain embodiment, a CASE assay can include any suitable probes for a particular assay. The anti-TAG antibodies can be provided on any suitable solid substrate. Reporter enzyme 139 can be any suitable enzyme, such as any of those discussed herein.

Optical Labeling

In certain aspects, the invention provides methods and devices for optical labeling of samples or assays. Methods of optical labeling include adding a dye to a sample or assay before droplet formation. Different samples or assays can be multiplexed by adding one dye at different concentrations.

FIG. 11A shows a plot in which the x-axis corresponds to the droplet assay signal and the y-axis corresponds to different concentrations of dye. As can be seen from FIG. 11A, fluid partitions can include dye in six different concentrations and still be clearly optically resolvable from one another. More than six different concentrations can be used such as, for example, seven, ten, fifty, or more.

Optical labeling can include further multiplexing by using additional dyes. For example, FIG. 11B shows a plot in which the x-axis shows 10 different concentrations of a dye that emits at 590 nm, while the y-axis shows 10 different concentrations of day that emits at 650 nm. By including two dyes at 10 concentrations each, 100 samples can be separately labeled and run through a single assay (99 samples are shown in FIG. 11B).

Multiplexing by these methods provides a high throughput readout. In certain embodiments, a single dye laser set allows for 6-7 or more (e.g., 10, 25, more) index levels per run. An additional laser then allows greater numbers (e.g., >30). By multiplexing at these levels, positive and negative controls can be run in an assay.

Figure 11C:
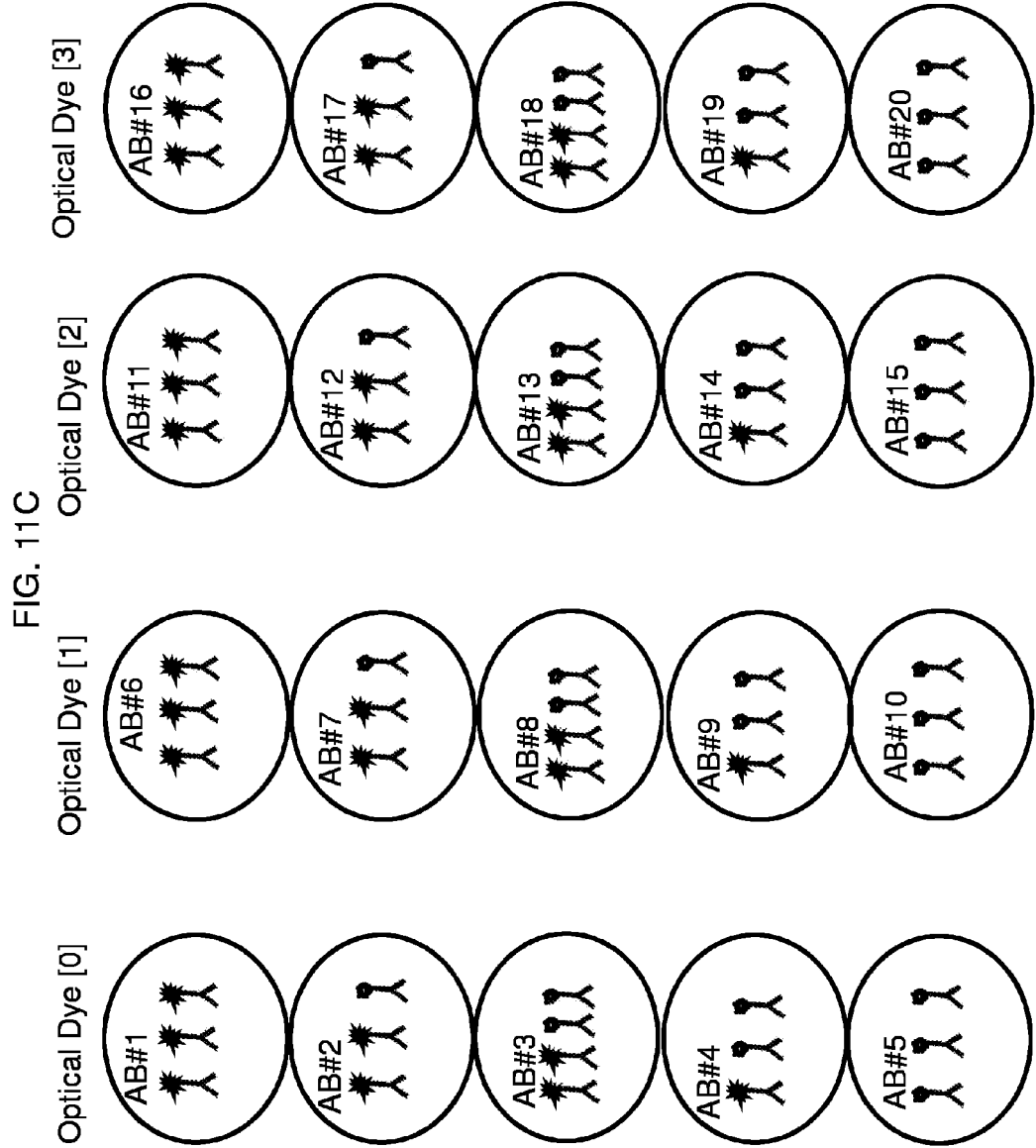

FIG. 11C shows the high levels of "plexity" for multiplexed reactions using different concentrations of an optical dye and different combinations of fluorescently labeled antibodies. As shown in FIG. 11C, each circle represents a fluid partition. Each inverted "Y" member represents an antibody. The labels "AB#1", "AB#2", . . . , "AB#20" refer to twenty different antibodies, and indicate that in any given fluid partition, all of the antibodies are the same. The antibodies are shown with two different fluorescent markers at their heads. A spiky marker indicates a first color (e.g., green), while a globular marker indicates a second color (e.g., red). "Optical Dye [1]" indicates a first dye concentration; "Optical Dye [2]" indicates a second dye concentration; "Optical Dye [3]" indicates a third dye concentration; and "Optical Dye [0]" indicates no dye.

Noting that in any given fluid partition in FIG. 11C all of the antibodies are the same, it can be seen that each fluid partition is nonetheless distinctly labeled by a combination of colored fluorescent markers and dye concentration. That is, no two partitions in one column contain the same combination of colors of fluorescent labels. Further, two different optical dyes can be included in each fluid partition, each separately detectable and each separately able to be provided at different concentrations. Imaging an idealized axis extending normal to the surface of FIG. 11C, it can be appreciated that a second optical dye provided in 3 distinct concentrations will allow the assay to be multiplexed with a "plexity" of 48—i.e., 48 different antibodies can be separately and distinctly labeled.

Localized Fluorescence

Figure 9A:
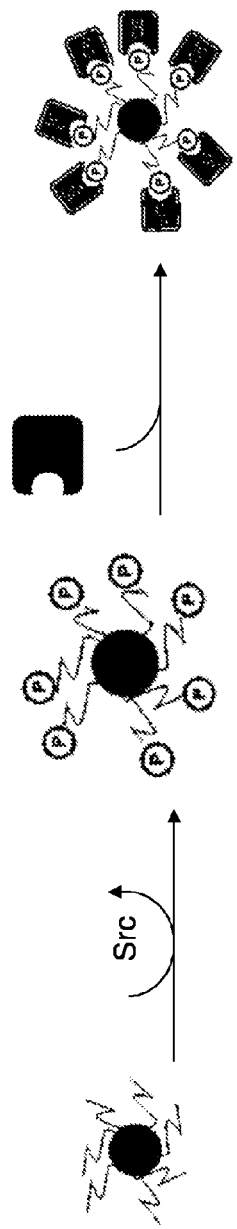
FIGS. 9A and 9B illustrate localized florescence as another mode for readout.
Figure 9B:
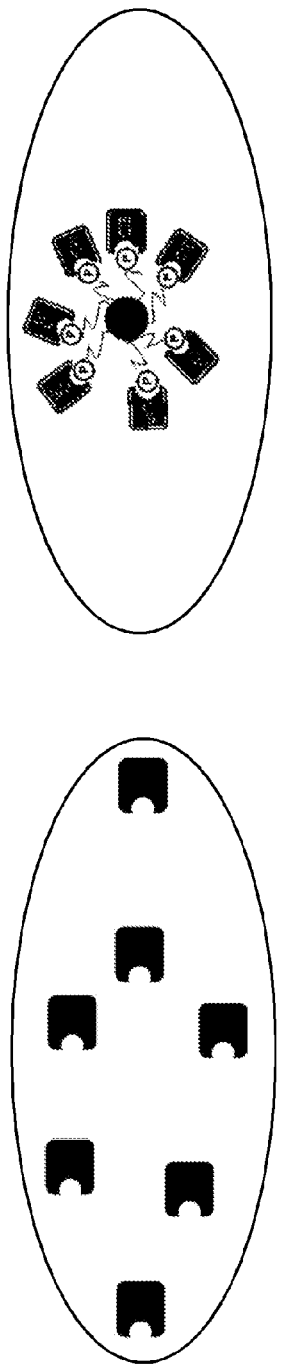

FIGS. 9A and 9B relate to methods of reaction detection in fluid partitions that employ a localized fluorescence method of detection. In these methods, positive (enzyme-containing) partitions are identified and counted using changes in the localized fluorescence of fluorescent molecules in the partitions. In general, methods of the invention employ any detection method that detects a localized concentration of a target in a fluid partition. For example, in certain embodiments, enzyme activity creates a binding surface for fluorescent molecules that can be monitored by localized fluorescent readout.

In the example shown in FIG. 9A, the enzyme Src kinase (Src) phosphorylates a Src substrate peptide that is immobilized on a bead. Phosphorylation of the Src substrate peptide creates binding motifs for the fluorescent reporter SH2-FITC. Thus, SH2-FITC binds to the bead-bound Src substrate phospho-peptide as shown in the last step of FIG. 9A.

FIG. 9B illustrates a reaction-negative fluid partition on the left side and a reaction-positive fluid partition on the right. Localization of the fluorescent molecules onto the bead surface can be detected as an increased signal on the bead surface, a decreased signal in a portion of the fluid partition (e.g., throughout the partition volume), or both. Many other enzymes, binding motifs, and fluorescent reporters can be used.

Any suitable method can be used to detect the pattern of localized fluorescence within a fluid partition. For example, in certain embodiments, fluid droplets are flowed through a narrow channel that forces the droplets to exhibit an elongated shape (as shown in FIG. 9B). As the droplets pass a laser detector, reaction-negative droplets give a uniform low-level fluorescence intensity along their length, while reaction-positive droplets show a spike corresponding to when the bead-bound fluorescent reporter passes the laser detector. In addition, when fluors become localized onto particle(s) within the droplet (e.g. on a bead or a cell surface) there is a coordinate depletion of the initial fluorescence in the regions of the droplet that do not contain the particle(s). Various signal processing algorithms can be used to combine local signal increases and background signal decreases into a more robust detection method.

Figure 12B:
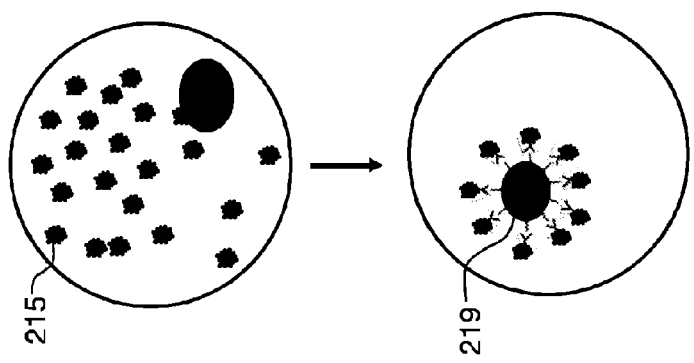
FIGS. 12A and 12B show a workflow for a localized fluorescence binding assay.
Figure 12A:
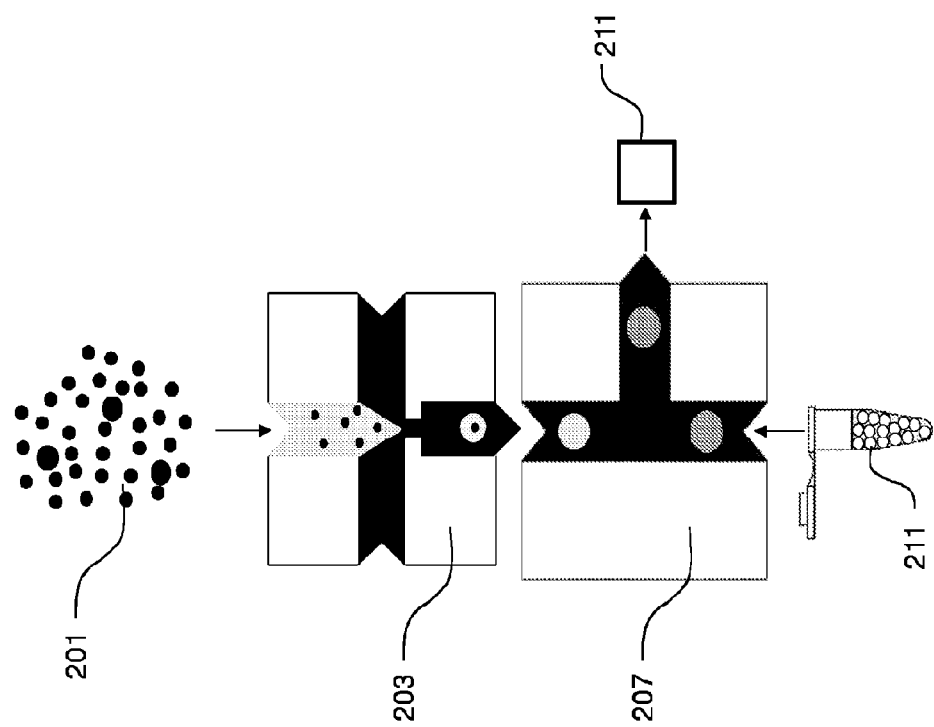

FIGS. 12A and 12B show a workflow for a localized fluorescence binding assay. Cell sample 201 provides cells that are flowed into droplet generator 203. An optically labeled library 211 (e.g., according to multiplexing embodiments discussed elsewhere herein) is flowed such that droplets from library 211 meet cell droplets from sample 201 in droplet merger 207. Droplets leave merger 207 having optical labels and reagents (e.g., fluorescent antibody to a biomarker of interest) and incubated (not shown) and then flow past detector 211. In certain embodiments, detector 211 includes a narrow channel portion 225 as discussed below in reference to FIG. 13. Libraries are discussed in U.S. Pub. 2010/0022414, the contents of which are hereby incorporated by reference in their entirety for all purposes.

FIG. 12B illustrates the principle of detection in detector 211. A fluid partition at the top of FIG. 12B includes a plurality of fluorescently labeled antibody 215 and a cell presenting an antigen of interest. After incubation, the fluid partition appears as at the bottom of FIG. 12B, where it is shown containing only one concentration of fluorescent marker 219, as all of the labeled antibody has bound to the cell.

Figure 13:
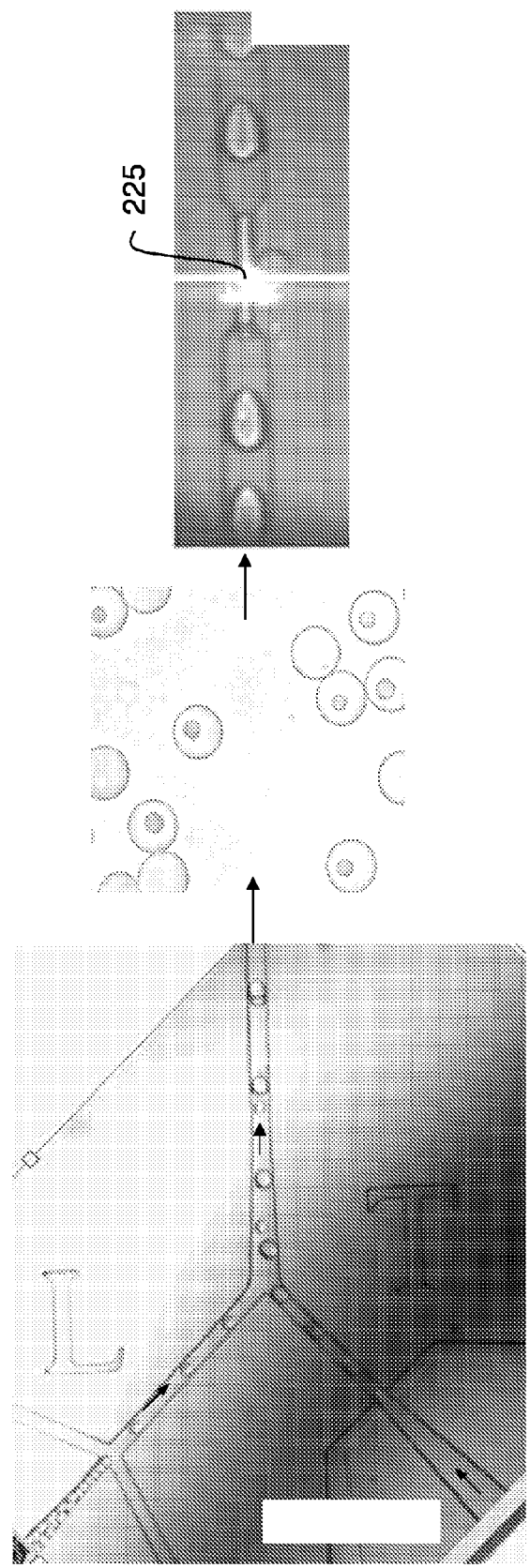
FIG. 13 shows monocyte detection according to certain embodiments.

FIG. 13 shows detection of CD45 on the surface of U937 monocytes with systems and methods of the invention. An optically labeled antibody library is flowed into the system from one input to merge with cells from the other (tracing the cell path across the figure from left to right). The streams merge and the droplets combine, after which the droplets are incubated "off chip", as indicated by the middle panel, in which the droplets can be seen without a surrounding microfluidic channel. After incubation, the droplets are flowed back onto a chip into a channel, after which they are flowed through narrow channel portion 225. Flowing through the narrow area causes the cells to elongate. A laser detector reads across the channel in the middle of narrow portion 225.

As the cells pass the laser, the detector detects fluorescence and creates a digital trace that can be stored and analyzed on a computer. The digital trace can be viewed on a display as a graph, in which the x-axis represents time (and corresponds to the length of the droplets as they pass the detector), and the y-axis corresponds to signal intensity (see example traces in FIGS. 14A-14C).

Throughput of the assay is adjustable and can be performed at, for example, about 1500 droplets per second (in the illustrated example, corresponding to about 150 cells/second). Incubation time (e.g., off chip, as shown in middle panel) can be adjusted. On chip, incubation can be adjusted by use of a delay line (i.e., wider portion of channel where flow slows). The interior diameter of narrow portion 225 can be adjusted to tune droplet elongation. For example, interior diameter can be about 10 micrometers or 15 micrometers.

In certain embodiments, localized fluorescence is used to screen for single-chain variable fragment (scFv) peptides in droplets. For example, a library of bacterially produced scFv's can be developed. Following a procedure as outlined in FIG. 12A, transformed bacteria cells 201 are encapsulated and incubated at 37° C. After incubation the droplets are combined with droplets that contain beads, antigens and a detection antibody from library 211.

The droplet based binding assays utilize localized fluorescence detection of scFv binding as shown in FIG. 12B. Specifically, the diffuse signal becomes bright and localized on the capture bead.

Positive droplets are detected according to a localized fluorescence method such as the one illustrated in FIG. 13. In order to get a reading of the droplet and fluorescent level therein, the droplet is elongated for detection in narrow channel portion 225 as shown in FIG. 13.

The positive droplets can then be broken and the contents recovered and sequenced. The process is able to screen for scFv's in droplets at a rate of about $1\times10^6$ per hour. Localized fluorescence and scFv screening is discussed in U.S. Pub. 2010/0022414, the contents of which is hereby incorporated by reference in its entirety.

Figure 14A:
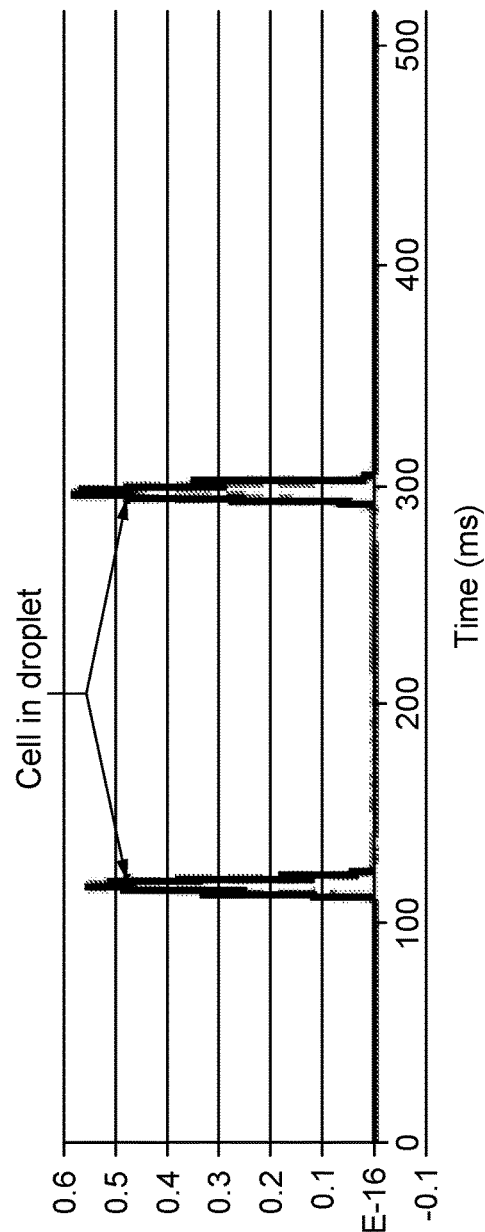
FIGS. 14A-14C illustrate single droplet traces including optical labels.
Figure 14B:
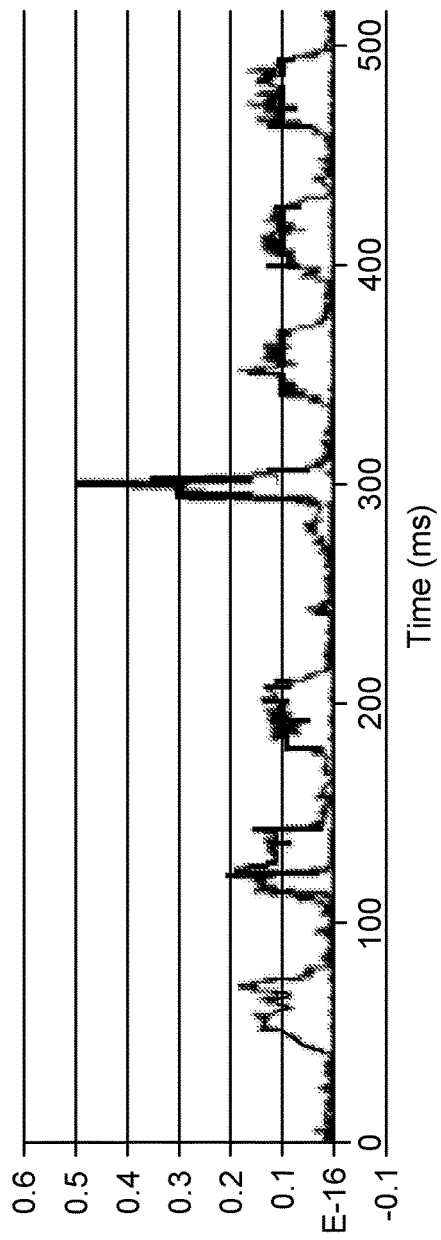
Figure 14C:
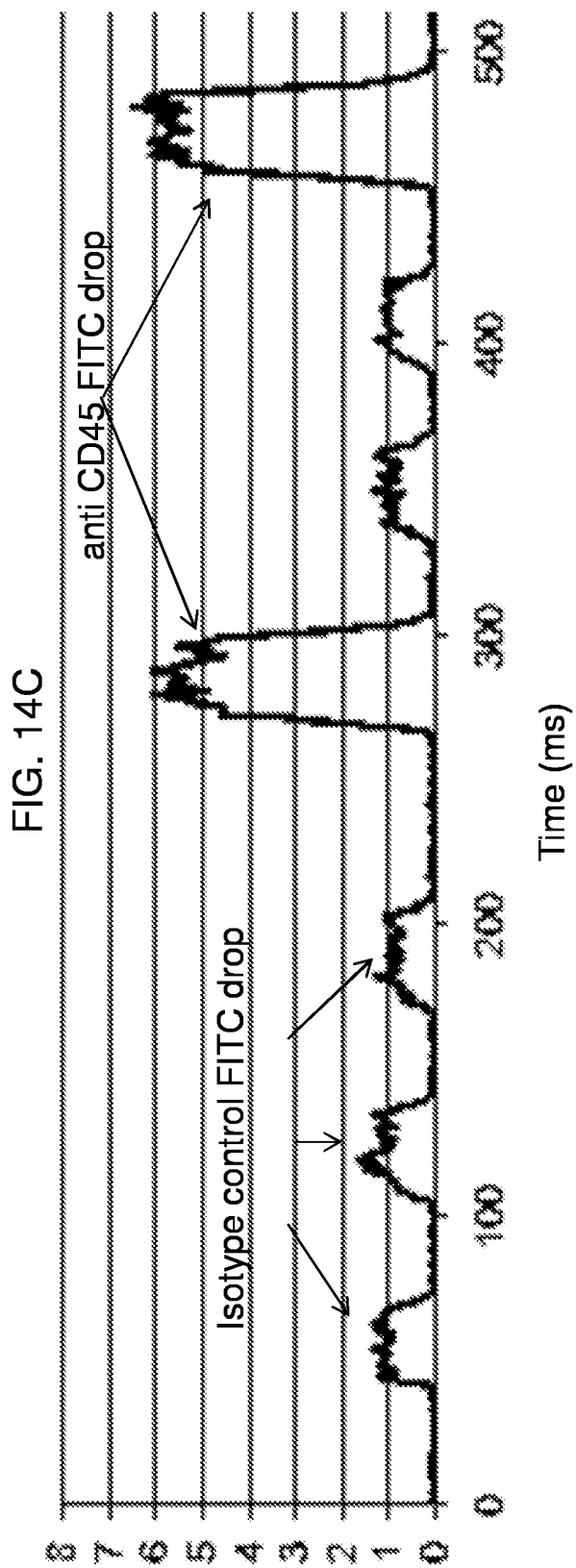

FIGS. 14A-14C illustrate single droplet traces including optical labels in a localized fluorescence assay. Note that the trace in each of FIGS. 14A-14C may be shown in a separate color for example on a single display. In each figure, the axes are the same and the traces can be obtained in a single run detecting three differently colored labels simultaneously. FIG. 14A shows a trace indicating measurement of cell viability stain. Here, calcein AM can be used, which gives a low intensity signal until it is cleaved by esterases located only inside a cell. The two spikes in FIG. 14A (at approximately 110 ms and approximately 300 ms) indicate the second and fourth droplets, respectively, to pass the fluorescent detector. These two spikes indicate that those droplets included a viable cell.

FIG. 14B shows a signal strength of FITC signal for droplets that include a labeled binder (e.g., anti-CD45-FITC). A spike (e.g., at 30 ms) indicates binding (i.e., a localized increase in fluorescence) while "bulges" centered on about 60 ms, 125 ms, 190 ms, 355 ms, 420 ms, and 480 ms (corresponding to the second, third, fourth, sixth, seventh, and eight droplets to flow past the detector, respectively) indicate dispersed, low-level fluorescence and thus indicate no binding. In conjunction with to FIG. 14A, which indicate the presence of a viable cell in the fourth droplet, FIG. 14B indicates that the viable cell is binding anti-CD45.

It will appreciated in viewing FIG. 14B that the spike at about 300 ms is surrounded by a low-level "bulge" spanning about 275 ms to about 320 ms. A positive assay can be detected by the low level of the signal across this "bulge" as compared to the signal level in the reaction-negative bulges (e.g., consistently above about 0.1). Thus, localized fluorescence can be detected (and positive or negative reaction fluid partitions identified) by localized increases of fluorescence, partition-wide decreases in fluorescence, or both. For example, a ratio could be calculated between the localized increase and the partition-wide decrease, and this ratio would be a sensitive indicator and/or measurement of localization within the partition. Moreover, measurement of the total volume of the partition may also be taken into consideration to further scale or normalize the partition-wide decrease.

FIG. 14C illustrates optical labeling that was included with the droplets shown in FIG. 14B (shown here as a blue trace). Here, control droplets were labeled with a low concentration of dye, while test droplets (including the anti CD45-FITC) were labeled with a high concentration of the dye. Thus, the first three signals, the fifth signal, and the sixth signal indicate that the corresponding fluid partitions are negative controls. while the fourth and seventh droplets were test partitions. An independent (e.g., downstream or upstream) channel can be used to count cells, count droplets, sort cells, or perform other steps.

Figure 15A:
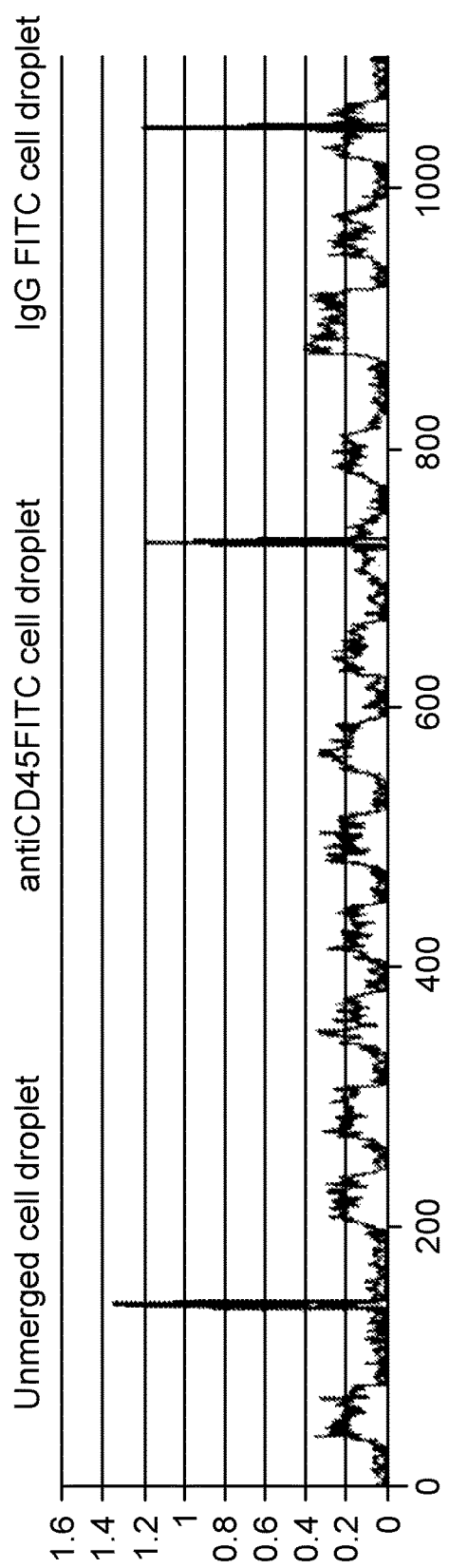
FIGS. 15A-15C give single droplet traces with a scatter plot and histogram.
Figure 15B:
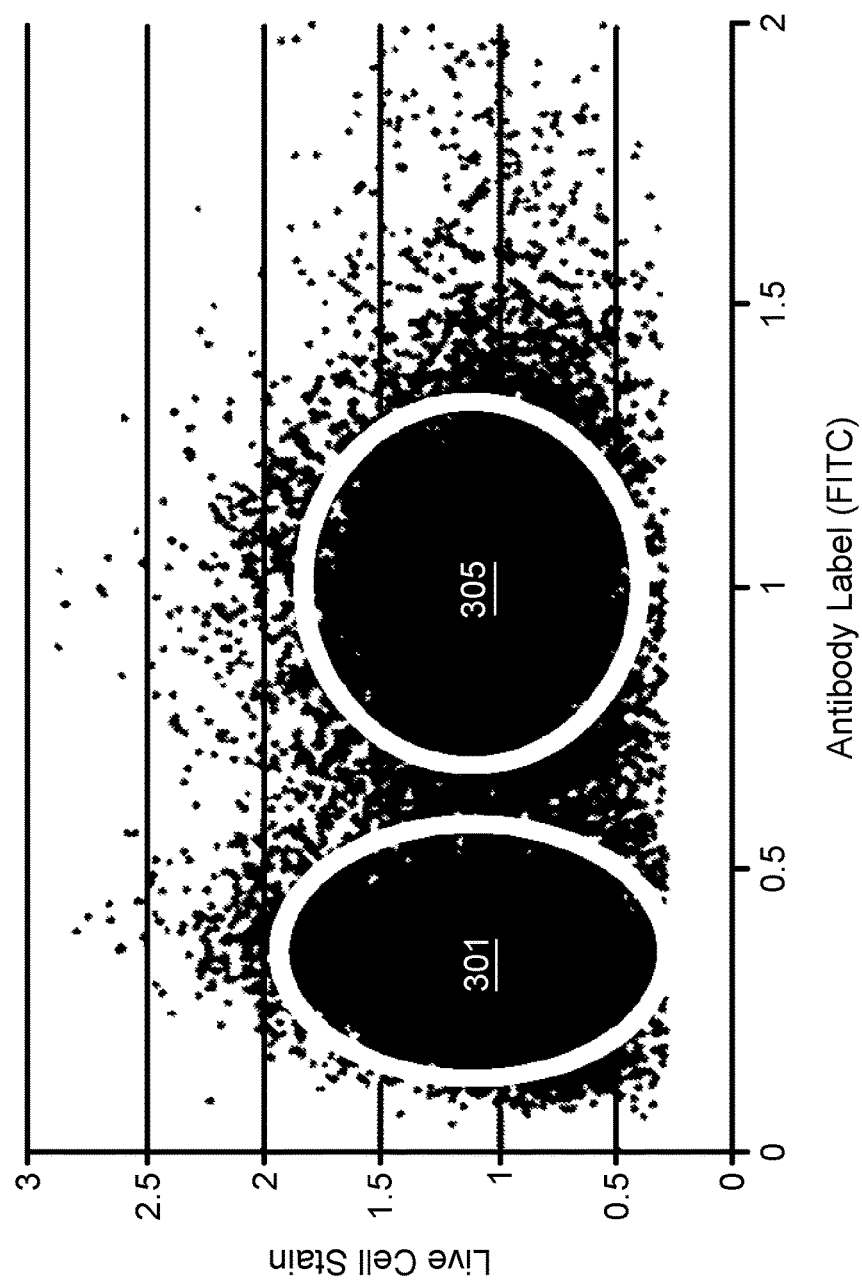
Figure 15C:
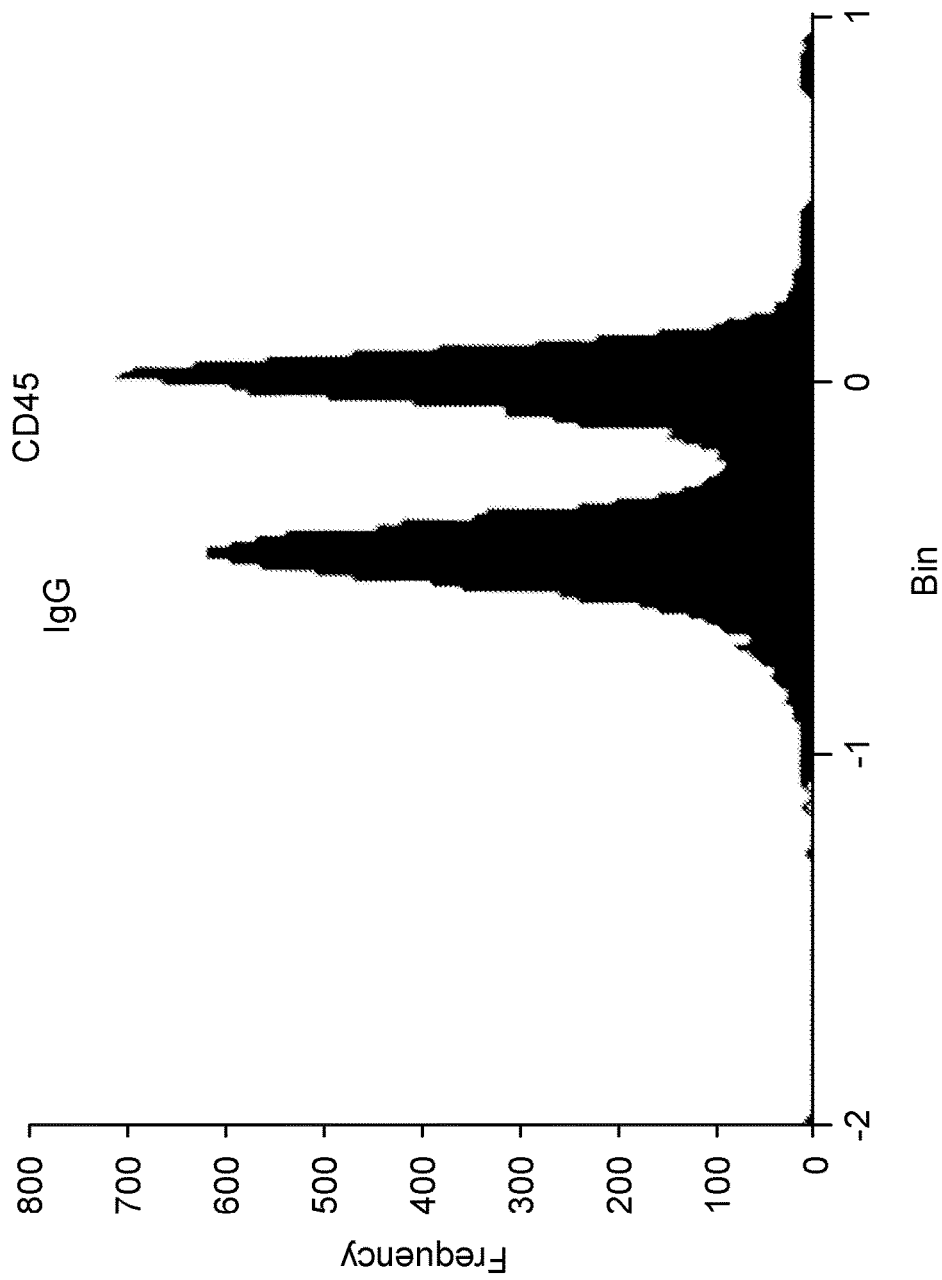

FIGS. 15A-15C give single droplet traces with a scatter plot and histogram. These figures illustrate the results of an assay for IgG and CD45. Here, two traces are superimposed. One trace indicates a level of fluorescence from FITC at locations within a fluid partition (similar to that shown in FIG. 14B). The other trace indicates a dye used in different concentrations to optically label the antiCD45 test partition distinctly from the IgG test partitions (i.e., the trace is similar to that in FIG. 14C). In FIG. 15A, the appearance of a signal at about 125 ms with no "shoulders" (i.e., lacking the trace that corresponds to FIG. 14B as discussed above) indicates a fluid partition that includes no FITC-labeled target. This indicates an unmerged cell droplet, i.e., a droplet that passed through merger 207 without receiving reaction reagents.

The signal at about 725 ms indicates an antiCD45-FITC positive droplet while the signal at about 1050 ms indicates an IgG-FITC positive droplet (the tenth and fourteenth droplets to pass the detector, respectively). Here, the tenth and fourteenth droplets are distinguished based on the concentration of the optical labeling dye (corresponding to the trace shown in FIG. 14C).

FIG. 15B gives a scatter-plot of results relating the traces shown in FIG. 15A. Along the x-axis is plotted an intensity of the antibody label and the y-axis corresponds to an intensity of a live cell stain. Population 305 corresponds to a CD45 positive population of fluid partitions and population 301 corresponds to an IgG positive population of fluid partitions. As unmerged droplets are also counted (e.g., second signal in FIG. 15A), the total number of droplets that is prepared can be accounted for. FIG. 15C shows a histogram corresponding to the plot shown in FIG. 15B. The x-axis is the unitless Bin and the y-axis is frequency. Such histograms are known in the art for display of flow cytometry results.

Figure 16A:
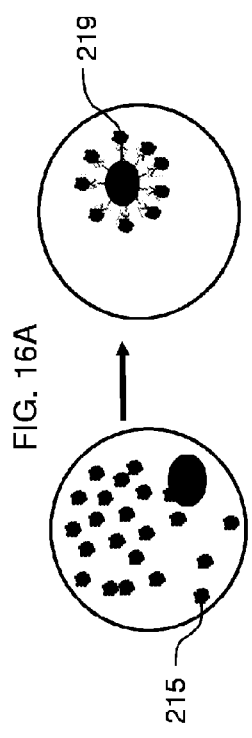
FIGS. 16A-16C diagram adjusting a dynamic range of a localized fluorescence assay.
Figure 16B:
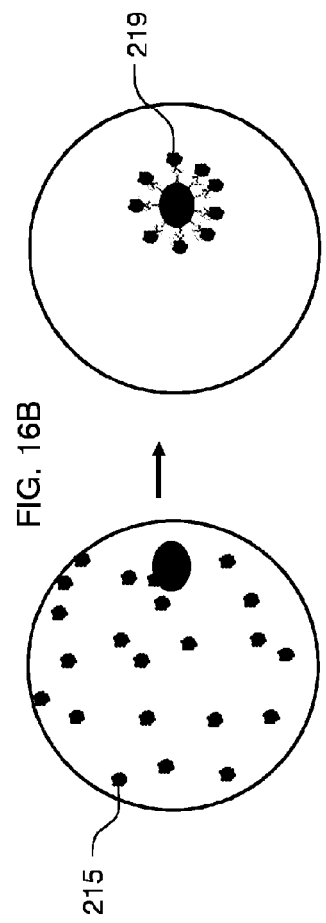
Figure 16C:
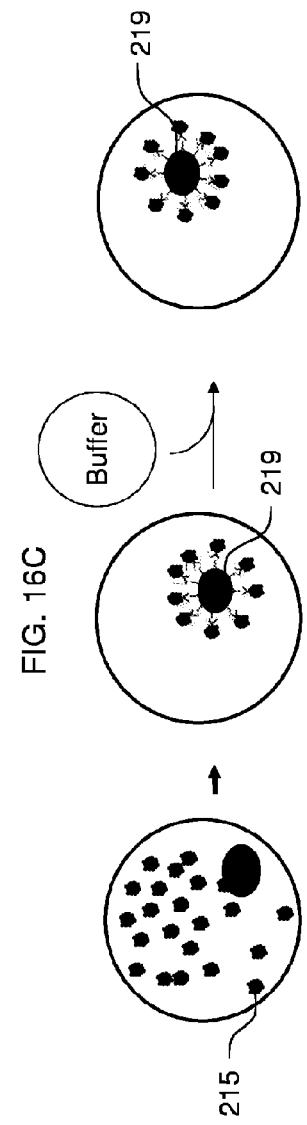

FIGS. 16A-16C show ways of controlling or adjusting the dynamic range of a localized fluorescence assay. As shown in FIG. 16A, an amount of fluorescently labeled antibody 215 can be provided in a determined relationship to a known or expected number of cell surface markers on cell 219. By controlling the concentration of antibody added (e.g., through a series of calibration runs), a desired signal of bound antibody can be established that is greater than the dispersed background signal.

FIG. 16B shows a method for lowering a strength of a background signal (shown to scale with the diagram shown in FIG. 16A). By making the fluid partitions larger, fluorescent antibody 215 will be more dispersed when in the unbound mode. However, when bound on cell 219, the bound signal will be substantially the same as between FIGS. 16A and 16B. Thus, by controlling a volume of a fluid partition, the signal gain can be modulated and the dynamic range of the assay adjusted.

FIG. 16C shows another way of adjusting the dynamic range by attenuating the background signal. Here, partitions included fluorescent antibody 215 are merged with partitions (only one is shown) that each contain at least one cell 219 (which may or may not be expressing the cell surface marker, i.e., positive and negative reaction partitions, where only positive is shown). A buffer is added to the fluid partitions. For example, droplets containing buffer are merged with assay droplets according to methods described herein. The buffer effectively dilutes the background signal. In certain embodiments, addition of the buffer does not substantially change the localized fluorescence signal (e.g., associated with reaction-positive instances of cell 219). The approach illustrated in FIG. 16C allows for a binding or incubation step to proceed at a substantially higher concentration (e.g., corresponding to concentration illustrated by left panel of FIG. 16A), while the detection step can employ a background (non-localized) fluorescence at a different concentration.

Localized fluorescence is applicable in combination with other assays and methods described herein including, for example, bead-capture based assays that involve rupturing or opening a partition to release the contents (as the signal may remain localized on the captured bead when it is, for example, but back into a fluid partition.

Digital Distribution Assays

In some aspects, the invention provides systems and methods for detecting distributions of molecules. For example, methods of the invention are useful to detect amounts of gene expression and proteins. In particular, methods of the invention are useful to detect protein aggregation or complexes. In one example, methods of the invention are used to detect anomalous or unexpected distributions of protein by conducting a chemical reaction that produces a detectable report indicative of the presence and amount of the protein (e.g., an ELISA or similar assay). The results of these assays are compared to expected results or control samples in order to determine whether there is an anomalous distribution or amount of a particular protein.

In certain embodiments, the invention is used to determine anomalous protein aggregation. In samples from the anomalous subset, peptide aggregation or complexes can be detected by the distribution of reactions in fluid partitions (e.g., digitally), as compared to the distribution from the non-anomalous rest of the population. Such a phenomenon may arise where a protein is known or suspected to exhibit alternative splicing, binding, or folding pathways or is in a stable complex. For example, one protein may be known to be differently processed (e.g., cleaved by hydrolysis or proteolysis; modified such as by phosphorylation; cross-linked; etc.) such that a complex or aggregate is formed when individuals have some disease propensity or state.

In Alzheimer's disease, for example, when amyloid precursor protein (APP) undergoes proteolysis, the resulting fragments can form aggregations such as fibrils. It is particularly hypothesized that a protein called tau becomes hyper-phosphorylated, causing the aggregation that results in neurofibrillary tangles and neuron disintegration. Thus, Alzheimer's disease may generally be associated with an aggregation of beta-amyloid protein. Accumulation of aggregated amyloid fibrils may induce apoptosis and may inhibit other critical enzyme functions.

This aggregation among proteins can result in there being an anomalous (e.g., non-Poisson) distribution of those proteins when assayed under dilution conditions which should produce Poisson-like statistic distributions, and this non-standard distribution can provide the basis for a digital detection assay.

Thus, digital assays are provided that relate to distributions of proteins and other cellular components. Assays according to methods of the invention involve determining an actual distribution and comparing that to an expected distribution.

FIG. 19 shows histograms corresponding to three different stages of protein aggregation. The histogram labeled "normal" indicates an expected distribution of proteins that are not aggregating. The histogram labeled "early" indicates a detected distribution in which proteins have started exhibiting aggregation. The histogram labeled "late" indicates a detected distribution of proteins that exhibit extensive aggregation.

Assays for digital distribution assays include any assay that can indicate a number of protein molecules per fluid partition. For example, where a protein has one epitope that is available while in either monomer or aggregated form, an assay can include antibodies bound to that epitope(s) coupled to reporters in each fluid partition. Each antibody can be linked (covalently or non, e.g., through biotin) to an enzyme. Each fluid partition is provided with fluorescently labeled substrate for the enzyme that fluoresces when the enzyme catalyzes a reaction on the substrate.

A sample is taken from a subject (e.g., a blood sample from a patient). Any desired concentration, isolation, or preparation steps are performed such that the target molecules become associated with a reporter for digital detection in partitions. The sample including the protein of interest and reporter is partitioned into fluid partition (this illustrative example is discussed in terms of a protein, but it will be appreciated that methods of the invention can detect a distribution of any target thus indicating aggregation or a complex).

Where the fluorescent reporter is the same for all antibodies, the number of proteins in each fluid is indicated by the fluorescent intensity of the signal. This can be run in "kinetic" mode, or "end point" mode. In end-point mode, each reaction is allowed to run to substantially completion, at which point the amount of product has substantially plateaued. The amount of product is then detected in each fluid partition and the number of proteins in each partition is correlated to the strength of the signal. The same correlation applies in kinetic mode. However, measurements are made at one or more time points before the amount of product plateaus. Where a whole series of time points is collect, that time series also gives information about enzyme kinetics.

In certain embodiments, where an assay is to be run in kinetic mode, a time point for measurement is first established in an independent calibration run. A series of droplets are made and incubated. The droplets are provided with a dilution of a protein that is known to aggregate and a reporter system (e.g., an enzyme-linked antibody that binds to an epitope of the protein). Fluorescence intensity is measured at multiple time points. For example, where measurement is on-chip and incubation is-off chip, all steps are performed at a temperature at which the enzyme exhibits no activity but incubation, which involves a temperature at which the enzyme exhibits activity. For example, β-gal exhibits no activity at 4° C., and is active at 37° C. For any given N-mer of aggregated protein, the fluid partitions that include one such N-mer will exhibit a characteristic sigmoidal time curve after a series of measurements of fluorescence are taken. To discriminate among some set of N-mers, a point along the time trace graph at which the corresponding sigmoidal time curves exhibit distinct heights is take for the measurement time.

In some embodiments, an expected distribution (i.e., from a healthy individual) is known, and an assay need only discriminate between a detected distribution and an expected distribution. Thus where, for example, an expected distribution has a known ratio of partitions that include 1 target to partitions that include more than one target, an assay can include detecting a ratio of partitions that include 1 target to partitions that include more than one target that is statistically significantly different than the known ratio. In some embodiments, a non-aggregating particle is expected to exhibit a Poisson or near-Poisson distribution, and an assay include detecting a number of droplets that contain greater than one target molecule, wherein the detected number does not agree with Poisson or near-Poisson distribution. In some embodiments, a Poisson distribution at a certain dilution is expected to yield a vanishingly small number of fluid partitions that include two target molecules and zero fluid partitions that include greater than two. Thus, an assay can detect a statistically significant number of partitions that includes more than one molecule to indicate the presence of protein aggregation and thus indicate the presence of a physiological condition. For reference, FIG. 3A shows a measurement result that may indicate protein aggregation (i.e., not match the expected distribution or Poisson).

In an alternative embodiment, each fluid partition is provided with enzyme linked antibodies in which all of the antibodies are the same, but a fraction (e.g., half) is linked to one enzyme that operates on one substrate to generate one reporter, and another portion of the antibodies are linked to another enzyme that catalyzes a reaction that produces a different reporter. In this example, assuming one reporter is blue and one is yellow, some number of fluid partitions that have more than one protein will produce both the blue and the yellow reporter. If the protein is not aggregating, at a certain dilution, it can be expected that blue and yellow will be found together in only some number of droplets (e.g., zero, or 0.00001% of them). In this example, detecting a blue with yellow in a greater number of droplets (e.g., 0.05%, 1%, etc.) indicates the protein is aggregating.

In distribution assays in which signal strength indicates a number of proteins in the droplet, for a given dilution of sample into droplets, assuming random distribution of a non-aggregating protein, there will be a characteristic expected distribution. Even for a protein that exhibits some aggregation in normal conditions, there will be a characteristic expected distribution. In certain embodiments, the expected distribution is predicted by Poisson or is Poisson-like. A substantially large number of droplets will contain zero proteins. A substantially majority of the droplets that contain any protein will contain 1 protein. Some small (maybe vanishingly small) number of protein-containing droplets will contain 2 or more.

In the case where the proteins aggregate, such an expected distribution will not obtain. For example, for a fully aggregated protein (e.g., "late" stage) that aggregates into 4-mers, a substantially large number of droplets will contain zero proteins and a substantial majority of the droplets that contain any protein will contain four proteins, as is illustrated in FIG. 19.

Furthermore, aggregation can be detected over time. That is, early stages of aggregation will exhibit an non-expected distribution. In some embodiments, protein folding into tertiary structures and/or quaternary assembly is studied over the course of, for example, minutes, hours, or days. In certain embodiments, a distribution of aggregation in a sample indicates a stage of progression of an aggregation-related condition that takes months, years, or decades to progress. For example, late stage distributions may only be expected after about 50 or 75 years. However, an assay run at an earlier time period (e.g., 15 or 25 years) may indicate an "early" stage aggregation distribution, as shown in FIG. 19.

In certain aspects, the invention provides a method for detecting a physiological condition in a human that includes forming fluid partitions that include components of a chemical reaction, in which at least one of the components has a detectable label that is acted on by the chemical reaction. The reaction proceeds in the partitions, and a number of reaction-positive partitions is identified and an amount of the component is determined. A statistically expected distribution or amount of the component is computed and compared to the actual distribution or amount. The results of the comparison can indicate the presence of an aggregation phenomenon.

In some embodiments, the invention provides a method for testing a response to a treatment for a condition or for monitoring a progression of a condition. A condition includes conditions that characterized by aggregation such as, for example, Alzheimer's disease. Determining a response to treatment is included in methods for development of treatments such as, for example, drug development. In some aspects, a candidate drug is tested (e.g., administered). A sample is taken and a distribution of molecules is determined. The molecules can be a protein such as beta-amyloid. Based on the determined distribution, an effectiveness of the drug is evaluated and a recommendation can be made. In some aspects, progress of a disease is monitored by methods that include taking a sample and determining a distribution of molecules within the sample according to methodologies described herein.

Digital distribution assays of the invention are highly sensitive and can proceed quickly with very small samples. For example, a 5 mL biological sample can be assayed in less than a day (e.g., about an hour), and a stage of aggregation can be determined.

In certain embodiments, the protein is beta-amyloid. A sample of human blood can be taken for the assay. An expected distribution can be calculated (e.g., statistically according to Poisson), derived empirically (e.g., sampling numerous members of a population for the majority pattern), or obtained from a reference such as a digital file or chart. Accordingly, in some embodiments, the invention offers a blood test for Alzheimer's disease. In certain embodiments, an assay of the invention can be performed on a patient at any life stage (e.g., childhood, teens, etc.). It will be appreciated that any aggregation pattern may be subject to detection by a digital distribution assay and aggregation generally includes the reverse phenomenon of fragmentation. As such, targets for a digital distribution assay may include peptides, nucleic acids, carbohydrates, lipids, or other molecules. A distribution assay can determine a stage of fragmentation as well as a stage of polymerization (e.g., esterification, poly peptide formation, carbohydrate cross-linking, synthetic polymerization, etc.).

Droplet Formation

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as U.S. Pat. No. RE41,780) and European publication number EP2047910 to RainDance Technologies Inc. The content of each of which is incorporated by reference herein in its entirety. Droplets can be formed with various uniform sizes, a non-uniform size, or a range of sizes.

Figure 17:
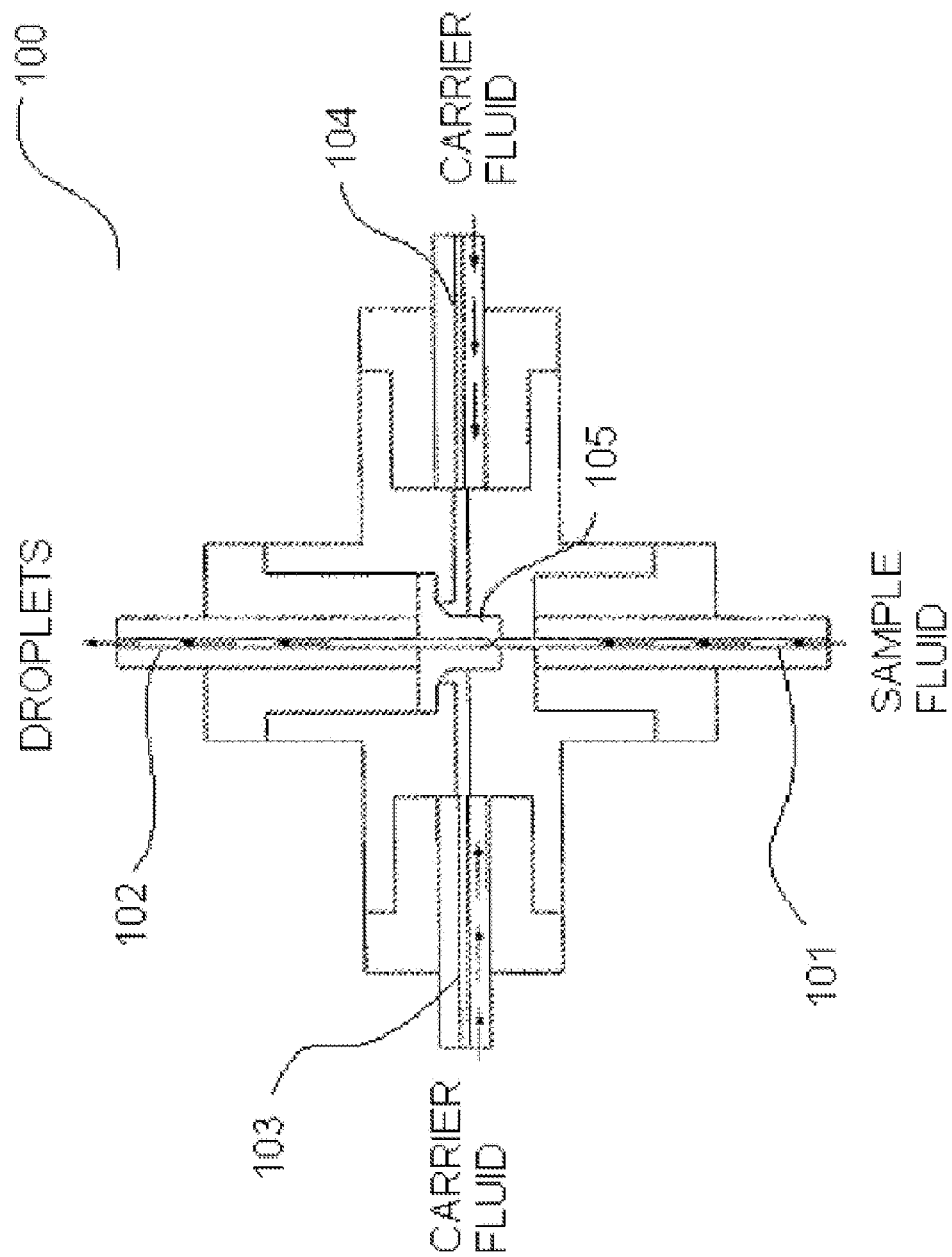
FIG. 17 is a drawing showing a device for droplet formation.
Figure 18:
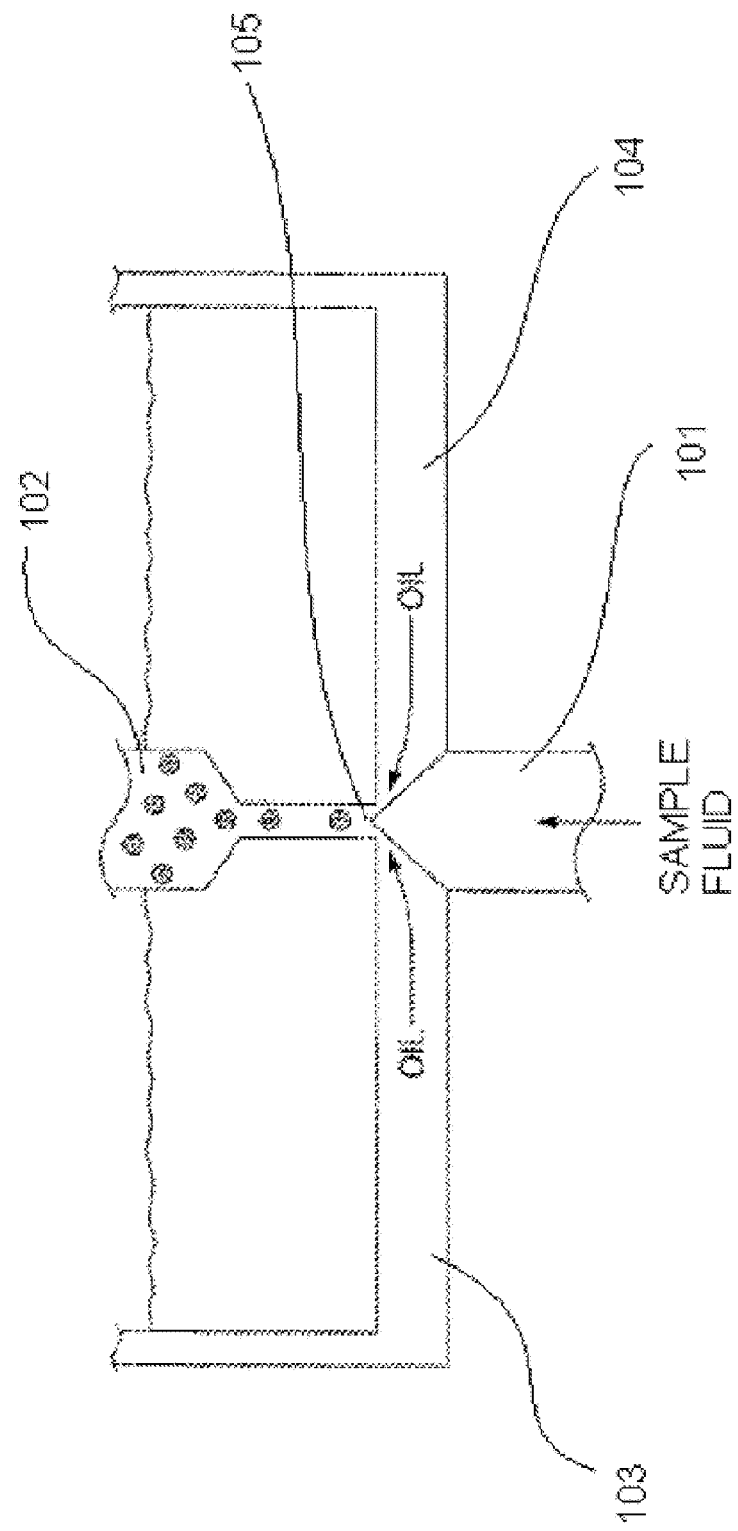
FIG. 18 is a drawing showing a device for droplet formation.

FIG. 17 shows an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 18). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with enzymes can be used. The carrier fluid is immiscible with the sample fluid. The carrier fluid can be a non-polar solvent, decane (e.g., tetradecane or hexadecane), fluorocarbon oil, silicone oil or another oil (for example, mineral oil).

In certain embodiments, the carrier fluid contains one or more additives, such as agents which reduce surface tensions (surfactants). Surfactants can include Tween, Span, fluorosurfactants, and other agents that are soluble in oil relative to water. In some applications, performance is improved by adding a second surfactant. Surfactants can aid in controlling or optimizing droplet size, flow and uniformity, for example by reducing the shear force needed to extrude or inject droplets into a channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt. %) in a fluorinated oil (e.g., Flourinert (3M)), which then serves as the carrier fluid.

Unknown or known analytes or compounds over a very wide dynamic range of concentrations can be merged with droplets containing single or multiple enzyme molecules and reporters via the use of a Taylor dispersion that forms upstream of the droplet forming nozzle. Co-encapsulation of an optical dye that has similarly been dispersed via a Taylor flow profile can be used to track the analyte/compound concentration. (see, e.g., Miller, et al., PNAS 109(2):378-383 (2012); U.S. Pat. No. 7,039,527; and U.S. Pub. 2011/0063943, the contents of which are hereby incorporated by reference in their entirety).

In certain embodiments, an aliquot of a sample is aspirated into a PEEK tubing, such that a slug of the sample is in the PEEK tubing with a substantially uniform concentration. The tubing is inserted into a port into a microfluidic channel, and the sample enters the channel forming a concentration gradient in the aqueous phase, the gradient generally following Taylor-Aris dispersion mechanics. The sample fluid joins the carrier fluid first having a vanishingly small concentration and then increasing up a gradient asymptotically until a maximum (e.g., 10 micromolar) is reached, after which it decreases similarly. The fluid is flowed to a droplet nozzle, where a series of droplets are made. The sample can be pushed into the channel via a pump, a plunger, or be driven by pressure (e.g., from a gas tank).

In certain embodiments, the dispersion is created for each partition of a plurality (e.g., for numerous or all wells from a 96 well plate, in which every well has a target sample such as a small molecule). Systems and methods of the invention provide a series of microdroplets in which the contents have a controlled concentration gradient through a simple injection procedure. Further, the sample can be spiked with a dye having a known concentration, and the dye concentration can be measured downstream (e.g., during or after any other assay). The measured dye concentrations can be used to determine the sample concentration.

By methods and systems provided here, a controlled gradient of concentrations of one or more sample aliquots can be merged with droplets that include a single target such as a single enzyme molecule. Enzyme activity can be assayed and kinetics studied. For example, individual enzyme molecules can be tested against a concentration range of activators, inhibitors, etc.

Substrates or other reaction or reporter components may be co-encapsulated into droplets with the enzyme without mixing before droplet formation by 'co-flow' of the separate components. When co-flow is used, each separate component is flowed to the microfluidic channel upstream of the droplet-forming nozzle, and both components flow in a laminar fashion to the nozzle without mixing. In co-flow methods, components are flowed in parallel streams through a channel. Due to flow dynamics, the contents of the streams do not mix until they hit the lambda injector or droplet forming nozzle. Two separate streams can be co-flowed, or three, four, or more. Where hardware is configured for N streams, and N−1 streams containing reaction components are desired, a "dummy" stream of water or saline can be included.

Another technique for forming droplets including enzymes and substrates from different fluids or previously generated droplets involves droplet merging. The merging of droplets can be accomplished using, for example, one or more droplet merging techniques described for example in Link et al. (U.S. patent application numbers 2008/0014589, 2008/0003142, and 2010/0137163) and European publication number EP2047910 to Raindance Technologies Inc. In embodiments involving merging of droplets, two droplet formation modules are used. A first droplet formation module produces the droplets including enzymes. A second droplet formation module produces droplets that contain substrate. The droplet formation modules are arranged and controlled to produce an interdigitation of droplets flowing through a channel. Such an arrangement is described for example in Link et al. (U.S. patent application numbers 2008/0014589, 2008/0003142, and 2010/0137163) and European publication number EP2047910 to Raindance Technologies Inc.

Droplets are then caused to merge, producing a droplet that includes enzymes and substrates. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/0014589, 2008/0003142, and 2010/0137163) and European publication number EP2047910 to Raindance Technologies Inc. Further description of producing and controlling dielectrophoretic forces on droplets to cause the droplets to merge is described in Link et al. (U.S. patent application number 2007/0003442) and European Patent Number EP2004316 to Raindance Technologies Inc. Additional methods may be used for controlled droplet merging, for example by altering the flow profiles of paired droplets via properly constrained microfluidic channel design. Merges can be performed in a successive fashion, enabling step-wise addition of substrates, reagents, or reaction step components.

Another approach to forming a droplet including enzymes and substrates involves forming a droplet including enzymes, and contacting the droplet with a fluid stream including substrate, in which a portion of the fluid stream integrates with the droplet to form a droplet including enzymes and substrates. In this approach, only one phase needs to reach a merge area in a form of a droplet. Further description of such method is shown in the co-owned and co-pending U.S. patent applications to Yurkovetsky, (U.S. patent application Ser. No. 61/441,985 and U.S. patent application Ser. No. 13/371,222), the content of which is incorporated by reference herein in its entirety.

A droplet is formed as described above. After formation of the droplet is contacted with a flow of a second sample fluid stream. Contact between the droplet and the fluid stream results in a portion of the fluid stream integrating with the droplet to form a droplet including nucleic acid from different samples.

The monodisperse droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. Preferably, the channels are oriented perpendicular to each other. However, any angle that results in an intersection of the channels may be used.

The bolus of the second sample fluid stream continues to increase in size due to pumping action of a positive displacement pump connected to channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet to form a mixed droplet. In certain embodiments, each incoming droplet of first sample fluid is merged with the same amount of second sample fluid.

In certain embodiments, an electric charge is applied to the first and second sample fluids. Description of applying electric charge to sample fluids is provided in Link et al. (U.S. patent application number 2007/0003442) and European Patent Number EP2004316 to Raindance Technologies Inc. (Lexington, Mass.), the content of each of which is incorporated by reference herein in its entirety. Electric charge may be created in the first and second sample fluids within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of bolus of the second sample fluid and the first sample fluid droplet. The forming mixed droplet continues to increase in size until it a portion of the second sample fluid breaks free or segments from the second sample fluid stream prior to arrival and merging of the next droplet containing the first sample fluid. The segmenting of the portion of the second sample fluid from the second sample fluid stream occurs as soon as the shear force exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel.

Droplet Sorting

Methods of the invention may further include sorting the droplets. A sorting module may be a junction of a channel where the flow of droplets can change direction to enter one or more other channels, e.g., a branch channel, depending on a signal received in connection with a droplet interrogation in the detection module. Typically, a sorting module is monitored and/or under the control of the detection module, and therefore a sorting module may correspond to the detection module. The sorting region is in communication with and is influenced by one or more sorting apparatuses.

A sorting apparatus includes techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A branch channel is a channel that is in communication with a sorting region and a main channel. The main channel can communicate with two or more branch channels at the sorting module or branch point, forming, for example, a T-shape or a Y-shape. Other shapes and channel geometries may be used as desired. Typically, a branch channel receives droplets of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In certain embodiments, a fluidic droplet is sorted or steered by inducing a dipole in the uncharged fluidic droplet (which may be initially charged or uncharged), and sorting or steering the droplet using an applied electric field. The electric field may be an AC field, a DC field, etc. For example, a channel containing fluidic droplets and carrier fluid, divides into first and second channels at a branch point. Generally, the fluidic droplet is uncharged. After the branch point, a first electrode is positioned near the first channel, and a second electrode is positioned near the second channel. A third electrode is positioned near the branch point of the first and second channels. A dipole is then induced in the fluidic droplet using a combination of the electrodes. The combination of electrodes used determines which channel will receive the flowing droplet. Thus, by applying the proper electric field, the droplets can be directed to either the first or second channel as desired. Further description of droplet sorting is shown for example in Link et al. (U.S. patent application numbers 2008/0014589, 2008/0003142, and 2010/0137163) and European publication number EP2047910 to Raindance Technologies Inc.

Droplet sorting relates to methods and systems described herein by allowing one to detect the effect of an enzymatic reaction in a fluid partition (or absence thereof) and to selectively examine that specific partition further. For example, where a specific class of molecule is being assayed for, an enzyme-positive droplet can be sorted and separated from the rest. That specific droplet can be "broken open" and its contents further examined. For example, a cDNA library can be prepared from all RNA (e.g., mRNA) in that droplet. Nucleic acids can then be sequenced.

Release from Droplets

Methods of the invention may further involve releasing the enzymes or products or other identifiable material from the droplets for further analysis. Methods of releasing contents from the droplets are shown for example in Link et al. (U.S. patent application numbers 2008/0014589, 2008/0003142, and 2010/0137163) and European publication number EP2047910 to Raindance Technologies Inc.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and further analyzed.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:
1. A method for quantifying enzyme molecules, the method comprising:
forming a plurality of fluid partitions comprising enzyme molecules and substrates in a microfluidic channel, wherein at least one substrate comprises a detectable label;

conducting an enzymatic reaction in at least one of the fluid partitions, wherein the detectable label is released; and quantifying the enzyme molecules by determining a number of fluid partitions that released the detectable label.

2. The method of claim 1, further comprising detecting a signal from the released detectable label in at least one fluid partition.

3. The method of claim 2, wherein the signal is measured by a laser detector.

4. The method of claim 1, wherein the step of forming comprises introducing a fluid stream comprising the substrates to a plurality of fluid partitions comprising the enzyme molecules.

5. The method of claim 1, wherein the at least one substrate is a fluorogenic substrate.

6. The method of claim 1, wherein the detectable label is a fluorescent polarization dye.

7. The method of claim 1, wherein the enzymatic reaction is conducted in an off-chip container.

8. The method of claim 1, wherein each fluid partition comprises no more than one enzyme molecule.

9. The method of claim 1, wherein each fluid partition comprises one or more substrates.

10. The method of claim 1, wherein the enzyme molecules are the same.

11. The method of claim 1, wherein the enzyme molecules are different.

12. The method of claim 1, wherein in the forming step, the plurality of fluid partitions further comprise a protein and at least one binding reagent.

13. The method of claim 12, further comprising incubating the plurality of fluid partitions.

14. The method of claim 12, wherein the protein is bound to two binding reagents.

15. The method of claim 14, wherein one of the binding reagents is immobilized.

16. The method of claim 15, wherein the binding reagent is immobilized on a magnet bead.

17. The method of claim 13, wherein the at least one binding reagent is an antibody.

18. The method of claim 14, wherein the protein is bound to the two binding reagents at different regions.

19. The method of claim 15, wherein the other binding reagent is biotinylated.

20. The method of claim 1, wherein one or more of the substrates are different.

21. The method of claim 1, wherein in the forming step, the enzyme molecules are each associated with a probe, wherein the probe is specific for a target nucleic acid.

22. The method of claim 21, wherein in the forming step, the enzyme molecules are associated with a plurality of different probes, wherein each probe is specific for a different nucleic acid.

23. The method of claim 22, wherein at least one probe comprises a tag.

24. The method of claim 23, wherein the tag has affinity to an antibody.

25. The method of claim 24, wherein the antibody is associated with a solid support.

* * * * *